United States Patent
Toles et al.

(10) Patent No.: US 8,123,718 B2
(45) Date of Patent: Feb. 28, 2012

(54) CHARGING MECHANISM FOR A NEEDLE FREE INJECTOR

(75) Inventors: Warren L. Toles, Clearwater Bay (CA); Kevin Toles, Winnipeg (CA); Jules Poiron, Somerset (CA)

(73) Assignee: Acushot Inc., Winnipeg (CA)

( * ) Notice: Subject to any disclaimer, the term of this patent is extended or adjusted under 35 U.S.C. 154(b) by 521 days.

(21) Appl. No.: 12/303,523

(22) PCT Filed: Jun. 7, 2007

(86) PCT No.: PCT/CA2007/001007
§ 371 (c)(1),
(2), (4) Date: May 11, 2009

(87) PCT Pub. No.: WO2007/140610
PCT Pub. Date: Dec. 13, 2007

(65) Prior Publication Data
US 2010/0004621 A1   Jan. 7, 2010

Related U.S. Application Data

(60) Provisional application No. 60/811,414, filed on Jun. 7, 2006.

(51) Int. Cl.
*A61M 5/30* (2006.01)
(52) U.S. Cl. .............. 604/70; 604/500; 604/68
(58) Field of Classification Search ............. 604/70, 604/500, 68, 69, 71, 72, 207–211, 140–147, 604/218–231
See application file for complete search history.

(56) References Cited

U.S. PATENT DOCUMENTS

| | | | | |
|---|---|---|---|---|
| 2,605,763 A | * | 8/1952 | Smoot | 604/70 |
| 3,951,038 A | * | 4/1976 | Van Langenhoven | 89/7 |
| 4,342,310 A | * | 8/1982 | Lindmayer et al. | 604/70 |
| 4,913,699 A | * | 4/1990 | Parsons | 604/68 |

(Continued)

FOREIGN PATENT DOCUMENTS
WO   2006/047087 A2   5/2006

OTHER PUBLICATIONS

Office Action dated Jan. 11, 2011 issued for Chinese Patent Application No. 200780028989.5.

(Continued)

*Primary Examiner* — Jackie Ho
*Assistant Examiner* — Michael J Anderson
(74) *Attorney, Agent, or Firm* — Lathrop & Gage LLP; James H. Velema, Esq.

(57) ABSTRACT

The present invention provides a needle-free injector for delivering a medicament under pressure into an animal or human, the injector having a charging mechanism comprising a threaded shaft/nut member combination. The injection device is of the type that includes an actuating device comprising: a gas tight chamber; a piston and rod assembly slidably received in the chamber and movable between a forward position and a rearward position; a gas charge in the chamber for urging the piston and rod assembly to the forward position; a mechanism for moving said piston and rod assembly against said gas charge into the rearward position; and a trigger for releasably retaining the piston and rod assembly in the rearward position. Also provided is a method and kit for using the device including the charging mechanism to administer a liquid through the skin of an animal or human.

22 Claims, 26 Drawing Sheets

U.S. PATENT DOCUMENTS

| | | | |
|---|---|---|---|
| 5,503,627 A | 4/1996 | McKinnon et al. | |
| 6,620,135 B1 * | 9/2003 | Weston et al. | 604/140 |
| 6,689,093 B2 * | 2/2004 | Landau | 604/69 |
| 6,689,101 B2 * | 2/2004 | Hjertman et al. | 604/131 |
| 6,974,446 B2 * | 12/2005 | Hommann et al. | 604/411 |
| 7,357,781 B2 * | 4/2008 | Menassa | 604/70 |
| 2002/0007142 A1 | 1/2002 | Hjertman et al. | |
| 2003/0225368 A1 * | 12/2003 | Landau et al. | 604/70 |
| 2004/0111054 A1 * | 6/2004 | Landau et al. | 604/68 |
| 2004/0249339 A1 * | 12/2004 | Willis et al. | 604/70 |
| 2004/0254526 A1 * | 12/2004 | Weston | 604/68 |
| 2005/0085767 A1 * | 4/2005 | Menassa | 604/68 |
| 2005/0192530 A1 * | 9/2005 | Castellano | 604/70 |
| 2005/0235975 A1 * | 10/2005 | Pedicini et al. | 124/67 |
| 2008/0319383 A1 * | 12/2008 | Byland et al. | 604/67 |

OTHER PUBLICATIONS

Austrian Search Report and Written Opinion for Application No. 200808963-3, dated Jul. 29, 2010.

* cited by examiner

A

B

Pressure pattern of inventive device

CHARGING MECHANISM FOR A NEEDLE FREE INJECTOR

RELATED APPLICATION

This application claims priority from U.S. 60/811,415, filed on Jun. 7, 2006, the entire contents of which are hereby incorporated by reference in their entirety.

FIELD OF THE INVENTION

The present invention pertains to the field of needle-free injectors. More particularly, the present invention pertains to the field of charging mechanisms for needle-free injectors.

BACKGROUND

Injections of medicaments are typically carried out using needle-containing injectors. There are a variety of problems associated with needle-containing injectors including cross-contamination of subjects receiving an injection, the pain associated with such injections and the potential for the needles to break, and dislodge, within a subject being injected. The breakage of a needle within a subject can be not only detrimental to the health and well-being of the subject, but can also have significant economic impact when the subject is livestock.

Increasingly, efforts have been directed to developing needle-free injectors, in attempts to avoid problems associated with needle-containing injectors in current use. Typically, such needle-free injectors are powered by an external gas supply so to provide sufficient energy to drive the liquid through the skin. The requirement of an external gas supply can be disadvantageous for the user, as it can be cumbersome and not amenable for use within an enclosure such as an office, laboratory, barn or the like. It can also be inconvenient to store of these types of external power supplies. Additionally, previous needle-free injectors are typically complicated in design, which in turn results in increased cost of manufacture.

There remains a need, therefore, for a charging mechanism for needle-free injectors.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a charging mechanism for needle-free injection device. In accordance with one aspect of the present invention there is provided a needle-free injection device for delivering a medicament under pressure from a dosing reservoir through an outlet orifice for administration to an animal or human, of the type comprising a plunger slidably received in said dosing reservoir and movable in a forward direction for expelling said medicament through said orifice, said injection device comprising an actuating device and said actuating device comprising: (a) a gas tight chamber; (b) a piston and rod assembly slidably received in said chamber and movable between a forward position and a rearward position; (c) a gas charge in said chamber for urging said piston and rod assembly to said forward position; (d) a charging mechanism for moving said piston and rod assembly against said gas charge into said rearward position, said charging mechanism comprising a threaded shaft threadingly engaged with a nut member that is operatively associated with said piston and rod assembly and moveable along a length of the threaded shaft when said threaded shaft is rotated; and (e) a trigger for releasably retaining said piston and rod assembly in said rearward position, whereby activating said trigger causes said piston and rod assembly to be released for movement by said gas charge to said forward position so as to impact said plunger directly or indirectly with a force sufficient to cause said plunger to move in said forward direction to expel said medicament through said outlet and whereby said gas tight chamber is adapted to minimize or prevent the escape of said gas charge so as to maintain said gas charge is a pressurized state.

In accordance with another aspect of the present invention, there is provided a method of injecting a medicament into an animal or a human, comprising: (i) providing an actuated needle-free injection device as described herein having a medicament within said dosing chamber; (ii) placing the outlet orifice against said animal at a site for administration; and (iii) triggering said injection device such that said medicament is expelled through said outlet orifice.

In accordance with another aspect of the present invention, there is provided a kit for the use of a needle-free injection device as described herein, comprising: (a) the needle-free injection device; and (b) instructions for the use thereof.

BRIEF DESCRIPTION OF THE FIGURES

FIG. 2A depicts the actuation device before being mounted in the housing of the needle-free injection device. FIG. 2 B depicts the actuation device mounted in the housing of the needle-free injection device, wherein the actuation device is in an uncharged condition. FIG. 2C depicts the same actuation device as depicted in FIG. 2B after charging of the device by the user, such that the piston and rod assembly is in the rearward position.

FIG. 3A depicts an exploded view of the plunger, gap-coupling and connector. FIGS. 3B and 3C depicts the plunger slidingly received within the gap-coupling, the gap-coupling is attached to the connector, which is in turn connected to the rod.

Figure 1:
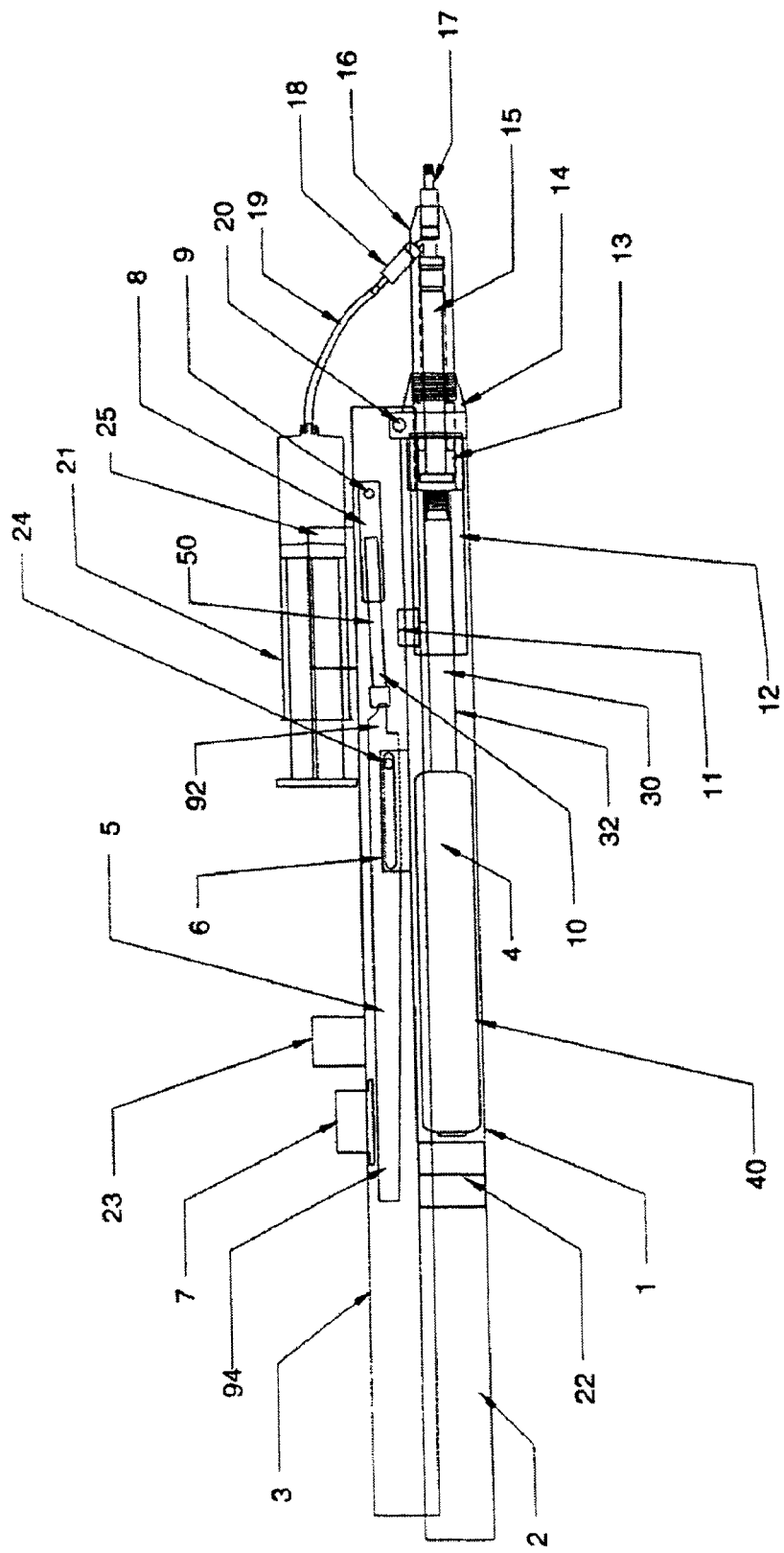
FIG. 1 is a cross-sectional view of a needle-free injection device according to one embodiment of the present invention.

In the Detailed Description that follows the numbers in bold face type serve to identify the component parts that are described and referred to in relation to the drawings depicting various embodiments of the invention. It should be noted that in describing various embodiments of the present invention, the same reference numerals have been used to identify the same or similar elements. Moreover, for the sake of simplicity, parts have been omitted from some figures of the drawings.

DETAILED DESCRIPTION OF THE INVENTION

As will be explained in more detail below, the present invention provides a needle-free injection device for injecting a medicament under pressure into a human or animal. The device of the present invention comprises some of the features of standard needle-free injection devices including a dosing reservoir for the medicament, and an outlet orifice in the dosing reservoir through which the medicament is expelled for administration to the animal or human. As in certain needle-free injection devices known in the art, the device of the present invention makes use of a plunger slidably received in the dosing reservoir and movable forward for expelling the medicament through the outlet orifice. In the device of the present invention, these features are combined with an actuating device comprising a gas tight chamber having a piston and rod assembly slidably received therein, a gas charge in the gas tight chamber for urging the piston and rod assembly to a forward position, means for moving the piston and rod assembly against the gas charge to a rearward position and a trigger for releasably retaining the piston and rod assembly in the rearward position, such that when the trigger is released, the piston and rod assembly moves to the forward position so as to impact the plunger, directly or indirectly, with sufficient force to move the plunger forward to expel medicament from the dosing reservoir and through the skin of the human or animal being treated.

All or a portion of the needle-free injection device is preferably sized to be portable, for example hand-held, thereby allowing a user to move from subject to subject (e.g., a human or an animal) to perform injections. Alternatively, all or a portion of the needle-free device may be permanently or removably attached to a structure, such as an injection station, thereby allowing the user to bring the subjects to the injection station to receive an injection. In certain applications it may also be beneficial to have only the dosing portion of the device sized to be hand-held by a user. In this embodiment, the actuating portion remains operatively associated with the dosing portion.

Referring to the Figures, the needle-free injection device comprises a dosing reservoir 16 for receiving a liquid, such as a medicament. Reservoir 16 has a discharge end having an outlet orifice having nozzle 17, through which the liquid in the reservoir may be expelled for administration to an animal or human. Optionally, nozzle 17 is removably attached to the discharge end of dosing reservoir 16, for example via a screw fit. Optionally, reservoir 16 has an inlet opening through which the liquid may be received. Dosing reservoir 16 can be sized to accommodate a range of volumes of liquid. Additionally, dosing reservoir 16 may be removable so as to facilitate the use of reservoirs of varied sizes and/or material suitable for different volumes or different liquids depending on specific applications.

Generally opposite the discharge end of the dosing reservoir is an expelling means for expelling the liquid within the dosing reservoir through the outlet orifice. In one embodiment of the present invention, as seen in FIG. 1, the expelling means is a plunger 15 slidably received in dosing reservoir 16 and movable between a rearward position and a forward position. Plunger 15 is sized to fit within dosing reservoir 16 such that when it is moved from the rearward position to the forward position it causes the liquid within dosing reservoir 16 to be expelled. Movement of plunger 15 from the rearward to the forward position is controlled by actuating device 40.

Actuating device 40 is disposed within a housing 1 of the needle-free injection device. Components of actuating device 40 are typically formed of a durable material, non-limiting examples of which include, steel, stainless steel and/or an alloy. Components of the needle-free injection device are typically formed of a durable material, non-limiting examples of which include, steel, stainless steel, an alloy, carbon fiber and/or composite plastic.

In accordance with one embodiment of this invention, housing 1 is adapted to be hand-held by a user, and is optionally adapted to receive an extension handle 2 via connector 22. Alternatively, actuating device 40 may be disposed on housing 1. Dosing reservoir 16 is optionally removably attached to housing 1, for example, via a screw fit.

In an alternative embodiment, housing 1 is not configured to be hand-held by a user but rather to be attached to a belt or held in a backpack, or the like, which is worn by the user. Alternatively, housing 1 is adapted to be removably attached to a structure. In each case, actuating device 40 remains operatively associated with the dosing portion of the needle-free injection device when in use.

Actuating Device

Actuating device 40 comprises a gas tight chamber 4 with a piston and rod assembly 32 reciprocally disposed within chamber 4 and moveable between a forward position and a rearward position. The term "gas tight chamber", as used herein, generally refers to a chamber having a piston and rod assembly reciprocally disposed therein. The gas tight chamber is adapted to minimize or prevent the escape of a pressurized gas, or mixture of gases, so as to maintain the gas, or mixture of gases, contained therein in a pressurized state.

Figure 2:
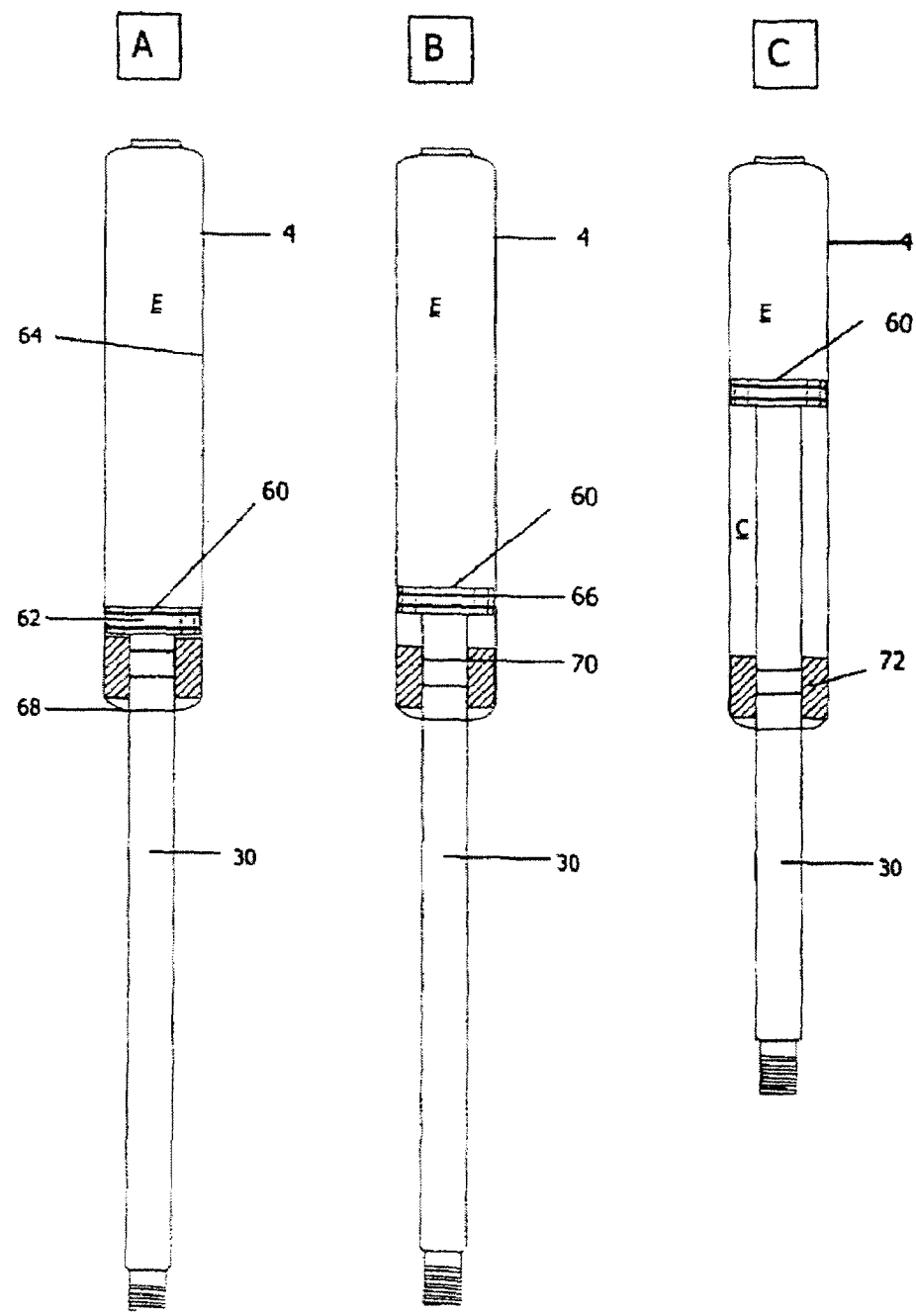
FIG. 2 provides three cross-sectional views of an actuation device in three stages of operation of a needle-free injection device according to one embodiment of the present invention.

Piston and rod assembly 32 includes piston portion 60 and rod portion 30. The shape of piston 60 generally corresponds to the shape of the interior of gas tight chamber 4. In a specific embodiment of the present invention, as depicted in FIGS. 2A, 2B and 2C, the gas tight chamber 4 is substantially cylindrical having an interior with a generally circular cross-section. Piston 60 of piston and rod assembly 32 is generally disk-shaped and the circumference of piston 60 defines an outer edge 62 that is in contact with the interior surface 64 of gas tight chamber 4 such that piston 60 defines an extension portion E and a compression portion C within gas tight chamber 4. The circumference of piston 60 may be defined by sealing member 66, which may be an o-ring. Piston 60 further comprises a through passage (not shown) for fluid communication between extension portion E and compression portion C. The passage is sized to enable rapid movement of piston and rod assembly 32 within chamber 4 from the rearward position to the forward position. This configuration is similar to that observed in conventional gas-charged springs or shock absorbers, wherein a passage(s) within the piston is sized to dampen or reduce the travel of the piston and rod assembly within the chamber.

In one embodiment, piston 60 has a generally circular passage therethrough having a diameter that is approximately one third (a ratio of 1:3) of the diameter of piston 60. The skilled worker will appreciate that the ratio of the diameter of the circular passage to the diameter of the piston 60 can be varied. If, for example, the ratio is 1:6, thereby having a smaller passage diameter as compared to the ratio of 1:3 mentioned above, the speed of the piston and rod assembly 32 would be decreased. This decrease in speed would allow for the use of a gas-charge, which would otherwise be used for a larger animal or humans, for injecting a smaller sized animal or human. In contrast, as the ratio approaches 1:1, the speed of piston and rod assembly 32 would be increased, as compared to the ratio of 1:3 mentioned above. In such a 1:1 configuration, gas-tight chamber 4 is constructed of sufficiently strong material to ensure piston and rod assembly 32 does not breach the end of the chamber 4 when moving to the forward position.

Rod 30 of piston and rod assembly 32 is disposed within chamber 4 and through opening 68 in chamber 4. Interaction of rod 30 with sealing means 70 positioned about opening 68 of chamber 4 provides a seal so as to minimize or prevent escape of the gas charge from chamber 4. In a specific embodiment, sealing means 70 is an o-ring.

In accordance with another embodiment of the invention, chamber 4 is provided with reinforcing members 72 positioned adjacent to opening 68. Reinforcing members 72 act to provide support to the walls of chamber 4 and to rod 30.

Chamber 4 contains a gas charge for urging piston and rod assembly 32 to its forward position (as shown in FIG. 2A). The term "gas charge", as used herein, generally refers to a pressurized inert gas, or a pressurized mixture of more than one type of inert gas, contained within gas tight chamber 4. Examples of inert gases suitable for use in the actuating device of the needle-free injection device of the present invention include, but are not limited to, nitrogen, carbon dioxide, helium, neon, argon, krypton, xenon, and mixtures thereof. Selection of the inert gas will depend on various factors, including: the application, cost, ease of use, etc. In practice, empirical tests can be used to confirm the suitability of a selected gas or gas mixture. In such tests, the suitability can be determined by measuring the depth of injection achieved in comparison to the depth when injection is performed with a traditional needle (an industry standard) and/or the recommended depth of medicament placement by medicament manufacturers. Advantageously, the inert gas is nitrogen. Conventional means of introducing a gas charge into chamber 4 can be used and are known to the skilled worker.

The pressure of the gas charge within gas tight chamber 4 is greater than that of the surrounding atmospheric pressure, thus urging the piston and rod assembly to the forward position (as shown in FIG. 2A). Ultimately, selection of the appropriate gas pressure and type of gas will depend on the application of the injection device. Advantageously, the pressure of the gas charge within the gas tight chamber is selected such that the medicament is expelled with a force of from 100 N to 2900 N. In an alternate embodiment, the pressure of the gas charge within the gas tight chamber is selected such that the medicament is expelled with a force of from 100 N to 5000N. As with certain currently used needle-free injection devices, the generated force can be adjusted, for example, by increments of 50 N (e.g., 100 N, 150 N, 200 N . . . 4550 N, 5000 N). However, it will be clear to the skilled worker that any force between 100 N and 5000 N can be selected depending on the force required to pierce the skin of the subject. The force can be adjusted by adjusting the pressure of the gas charge.

As piston and rod assembly 32 is moved from the forward position to the rearward position, the pressure of the gas acting to urge piston and rod assembly 32 forward increases. The repulsive force of the compressed gas on piston and rod assembly 32 is related to the pressure of the gas charge and the surface area of piston and rod assembly 32 exposed to the compressed gas.

In accordance with an embodiment of the present invention actuating device 40 includes a lubricating medium for lubricating the interaction of piston and rod assembly 32 and the interior of chamber 4. The lubricating medium may also enhance the sealing interaction between rod 30 of piston and rod assembly 32 and o-ring 70 in opening 68 of chamber 4. The loss of the gas charge and/or lubricating medium from chamber 4 is minimized or prevented due to the sealing interaction of rod 30 and sealing means 70. It will be appreciated by those skilled in the art that the nature of the lubricating medium, if present, depends on the overall application of the actuating device 40, and the conditions in which it is used. In one example, the volume and viscosity of the lubricating medium is selected such that the movement of piston and rod assembly 32 from the rearward position to the forward position within gas-tight chamber 4 is not significantly dampened by the presence of the lubricating medium. For example, a small volume of light weight oil is less likely to dampen the travel of the piston and rod assembly 32 than a larger volume or a heavier weight oil. In contrast, if the skilled user requires that the velocity of piston and rod assembly 32 be dampened (which may be necessary if, for example, a high pressure gas-charge is to be used), a greater volume and/or more viscous oil is used.

When the actuation device is installed in a needle-free injection device, the piston and rod assembly may be slightly compressed, as shown in FIG. 2B. This slight compression aids in distribution of the lubrication medium around piston and rod assembly 32.

In accordance with an alternate embodiment of the present invention, actuation device 40 is a modified version of commercially available gas spring (for example, such as from Standfast Industries).

In one embodiment of the present invention, actuating device 40 is disposed within a guide tube, which is connected to dosing reservoir 16 via a connector. The connector is a generally open-ended cylinder that has a first end, for removable attachment to the guide tube, and a second end, for removable attachment to dosing reservoir 16. Optionally, the connector is removably attached to the guide tube via a threaded connection. Similarly, the connector is optionally removably attached to dosing reservoir 16 via a threaded connection.

In an alternative embodiment, the connector is removably attached to dosing reservoir 16 via a quarter-turn release mechanism. In such a quarter-turn release mechanism, the connector further includes two pins projecting from the inner surface of the connector. In this example, dosing reservoir 16 includes a generally L-shaped groove in its outer surface. The protruding pins and generally L-shaped groove are configured to slidingly mate with each other when dosing reservoir 16 is inserted into the connector, and rotated, such that the pins follow the generally L-shaped groove. In the quarter-turn release mechanism, a barrel wave spring can be disposed between the connector and dosing reservoir 16 so as to urge the connector and dosing reservoir 16 apart, and prevent free rotation of the connector and dosing reservoir 16.

Gap Coupling

Figure 3:
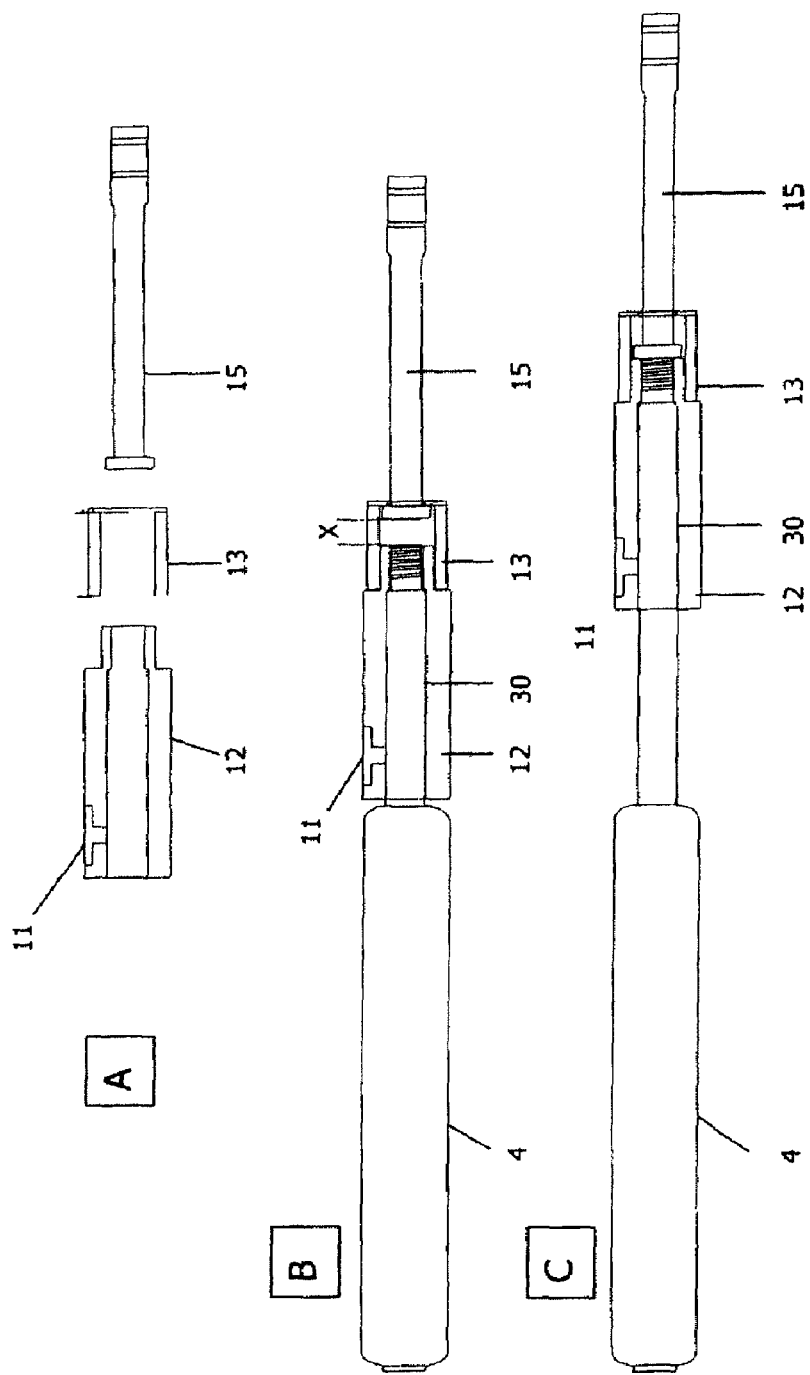
FIG. 3 is a cross-sectional view of a gap-coupling suitable for use in a needle-free injection device according to one embodiment of the present invention.

In one embodiment of the present invention, the actuating portion and the dosing portion of the injection device are directly attached to one another. In this embodiment, gap-coupling 13 connects rod 30 of piston and rod assembly 32 to plunger 15. Gap-coupling 13 maintains a gap-distance X between rod 30 and plunger 15 when piston and rod assembly 32 is in the rearward position. Gap-coupling 13 is removably attached to rod 30 and is in sliding engagement with plunger 15. As depicted in FIGS. 3A, 3B and 3C, plunger 15 is fitted through an opening in gap-coupling 13, such that plunger 15 is slidingly received within one end of gap-coupling 13. Gap-coupling 13 is attached at the opposite end to connector 12, which is, in turn, connected to rod 30. In an alternative embodiment, gap-coupling 13 is attached directly to piston and rod assembly 32 and no connector is required. It will be apparent to the skilled worker that gap-coupling 13 can be connected to rod 30 and plunger 15 in a variety of ways, provided that the gap-distance X is maintained between piston and rod assembly 32 and plunger 15 when piston and rod assembly 32 is in the rearward position. This configuration results in "direct" impact of plunger 15 by piston and rod assembly 32 when it is released for movement by said gas charge to its forward position.

Figure 4:
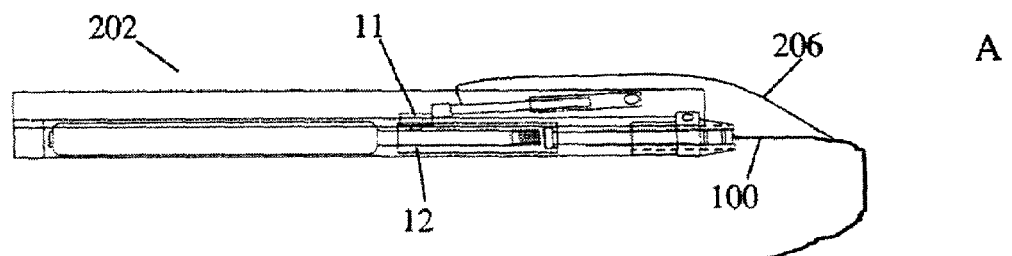
FIGS. 4A and B are cross-sectional views of a needle-free injection device (A) and a hand-held unit (B) according to one embodiment of the present invention.
Figure 4:
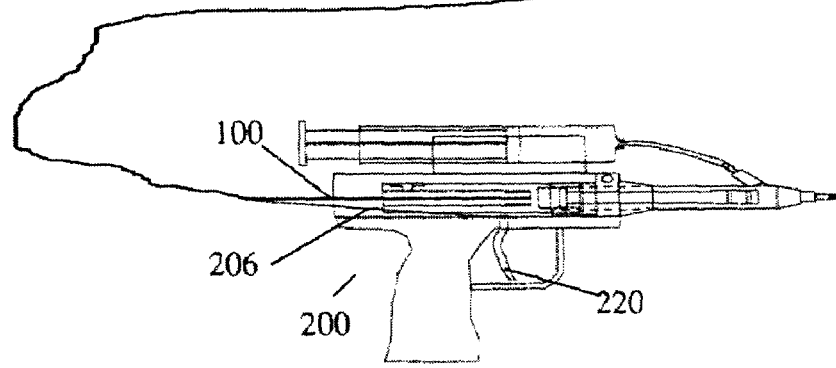
Figure 4:
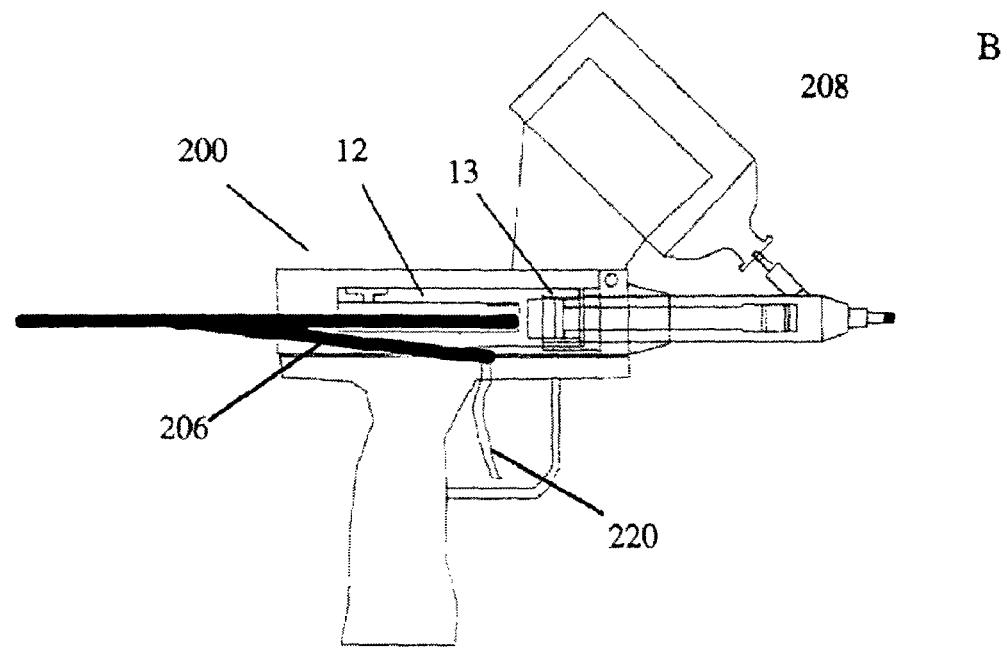
Figure 5:
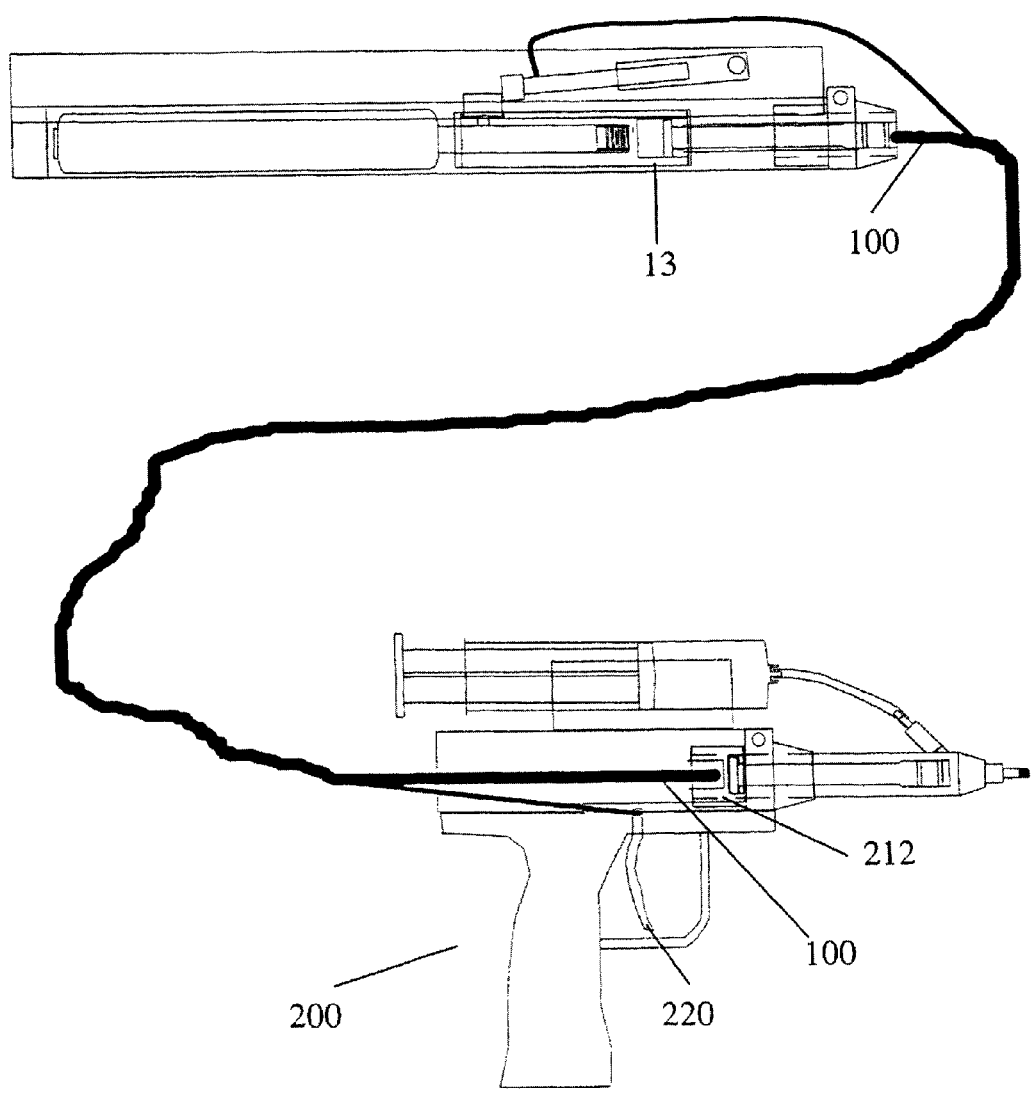
FIG. 5 is a cross-sectional view of a needle-free injection device according to one embodiment of the present invention.

In some instances, it may be desirable for the actuating portion of the injection device to be located apart from the dosing portion (see FIGS. 4 and 5). This can be advantageous, for example, if the actuating device is heavy and, therefore, it is easier for a user to carry the actuating portion at their waist, back, slung over a shoulder, or the like, in a remote portion 202. In this embodiment, hand-held portion 200 contains dosing chamber 16, plunger 15 and nozzle 17. In such a configuration of the needle-free injection device, transferring means 100 for transferring force generated by movement of piston and rod assembly 32 to said plunger 15 is incorporated into the overall device. This configuration results in "indirect" impact of plunger 15 by piston and rod assembly 32 when it is released for movement by said gas charge to its forward position. Specifically, activation of the trigger causes piston and rod assembly 32 to be released for movement by said gas charge to the forward position thereby imparting a force to transferring means 100, which in turn transfers the force to plunger 15. In such an example, gap-coupling 13 connects transferring means 100 to plunger 15 (FIG. 4), or rod 30 of piston and rod assembly 32 to transferring means 100 (FIG. 5). Gap-coupling 13 maintains gap-distance X between transferring means 100 and plunger 15 (FIG. 4), or between rod 30 and transferring means 100 (FIG. 5), respectively, when piston and rod assembly 32 is in the rearward position. Transferring means 100 can be in the form of, for example, a closed hydraulic hose, a flexible multi-link cable/shaft enclosed in a casing, or the like.

Figure 6:
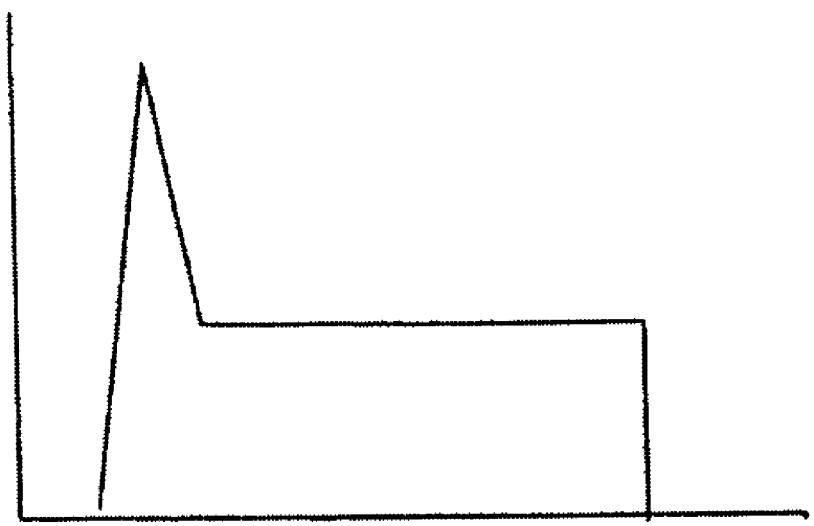
FIG. 6 is a graphical representation of the pressure pattern observed after triggering the injection device of the present invention.
Figure 7:
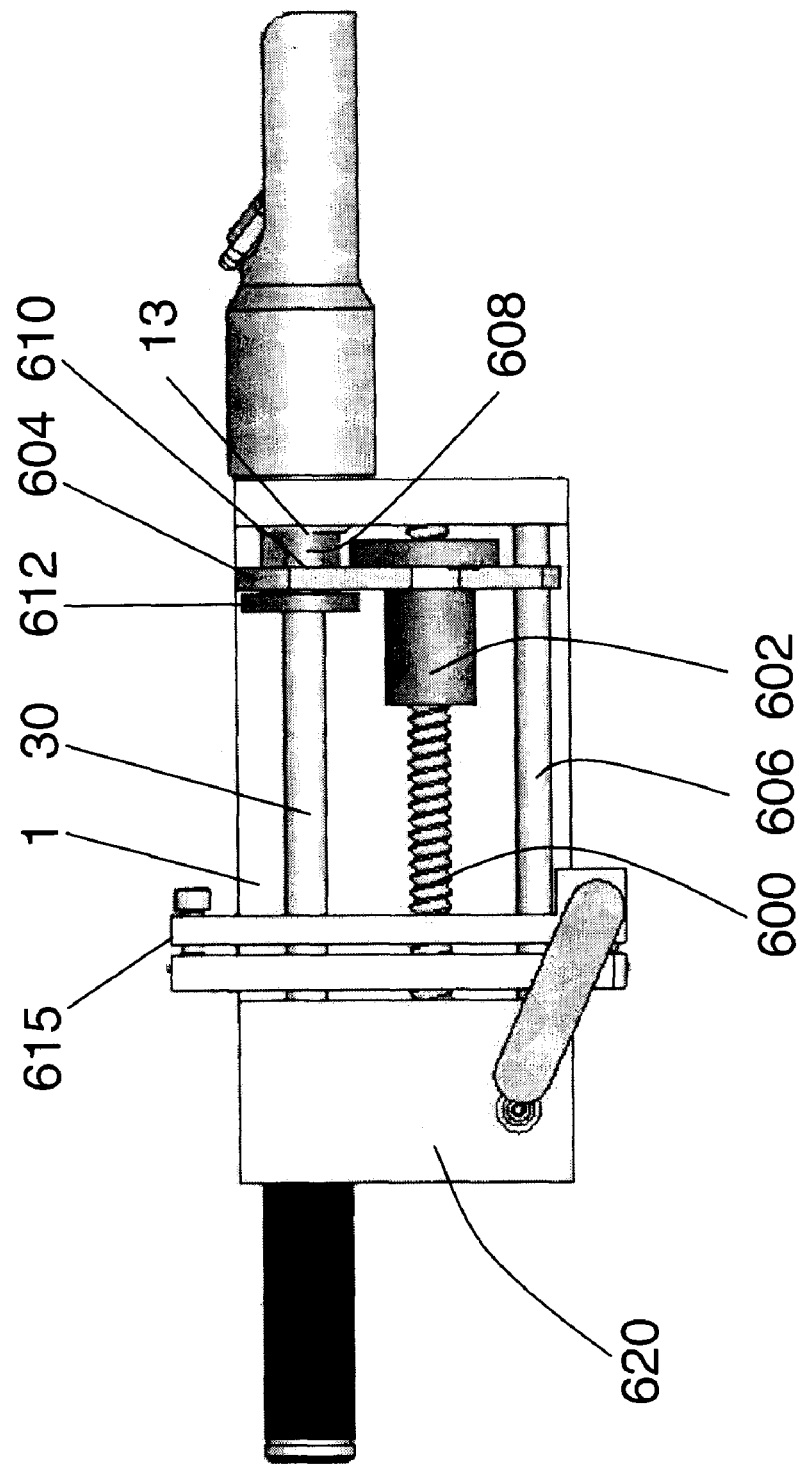
FIG. 7 is a side view of a needle-free injection device according to one embodiment of the present invention, showing the charging mechanism in the forward position.
Figure 8:
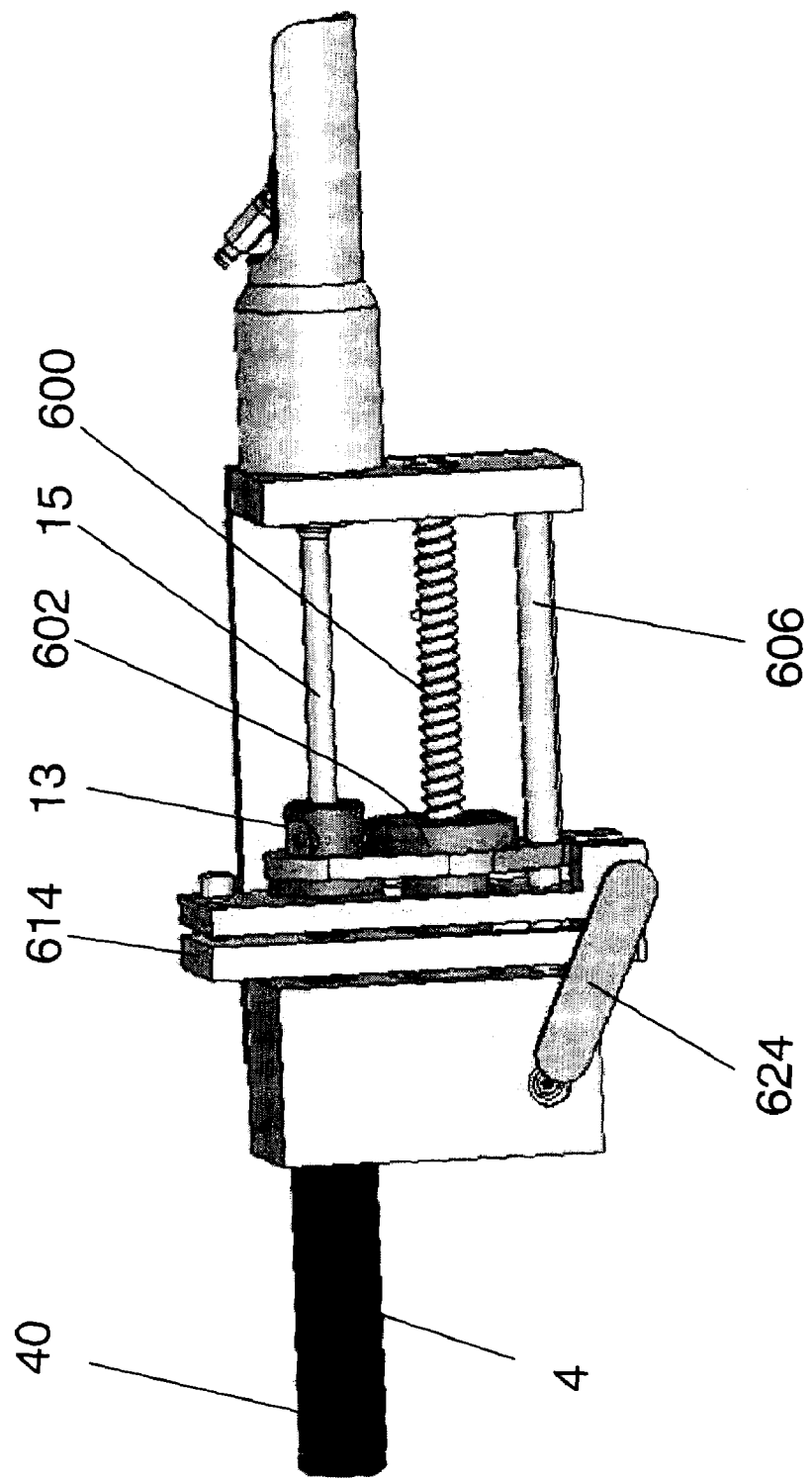
FIG. 8 is a perspective side view of the needle-free injection device of FIG. 7, showing the charging mechanism in the rearward position.
Figure 9:
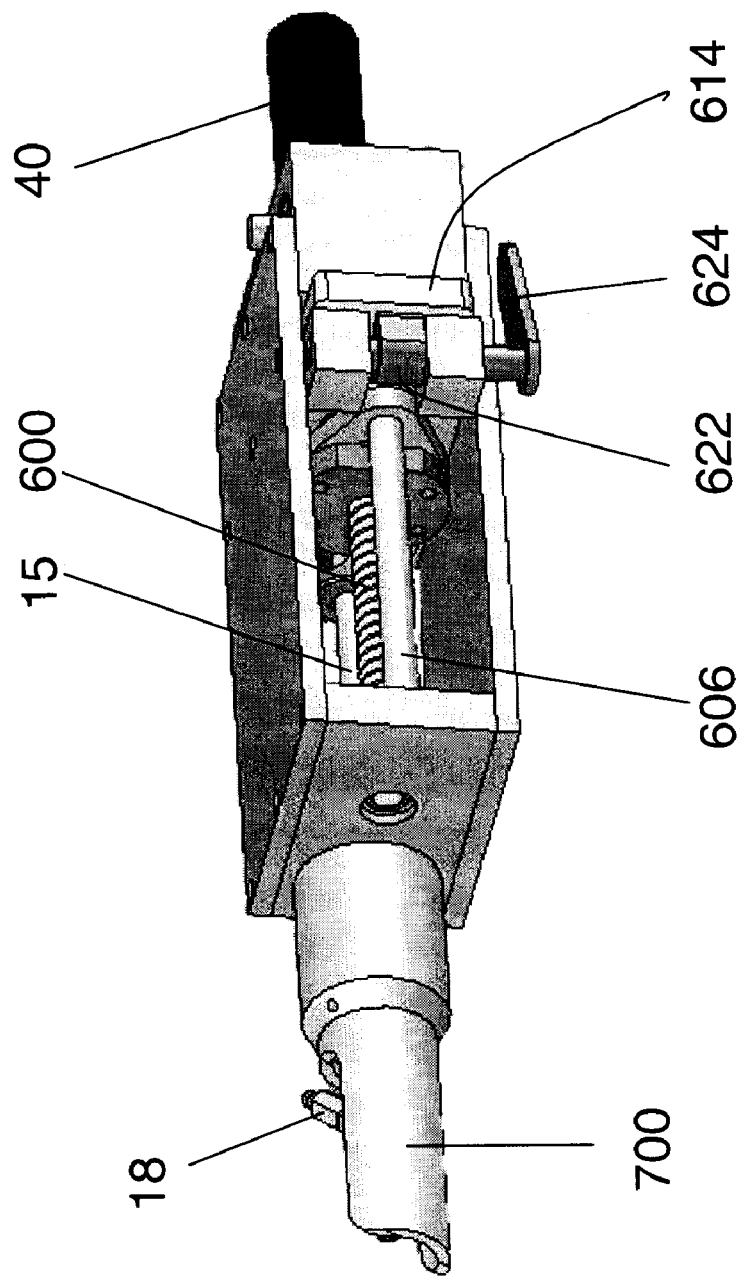
FIG. 9 is a perspective bottom view of the needle-free injection device of FIG. 7, showing the charging mechanism in the rearward position.
Figure 10:
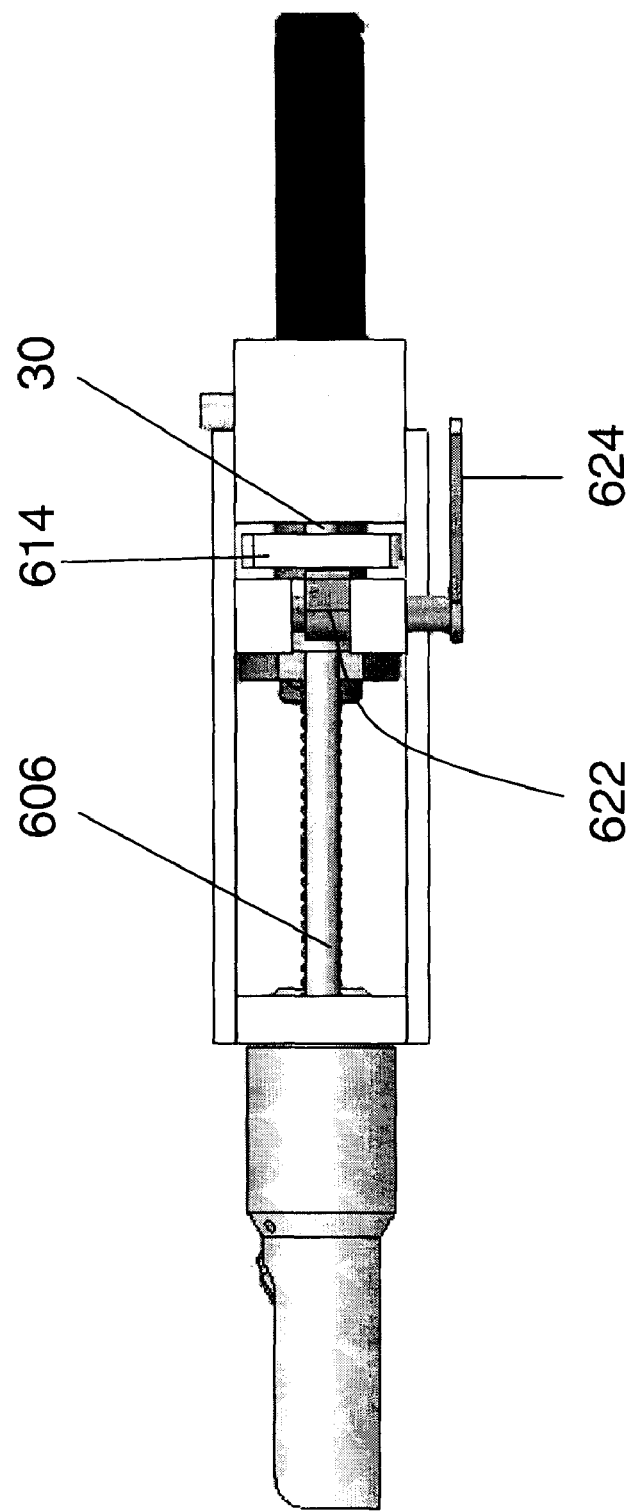
FIG. 10 is a bottom view of the needle-free injection device of FIG. 7, showing the charging mechanism in the rearward position.
Figure 11:
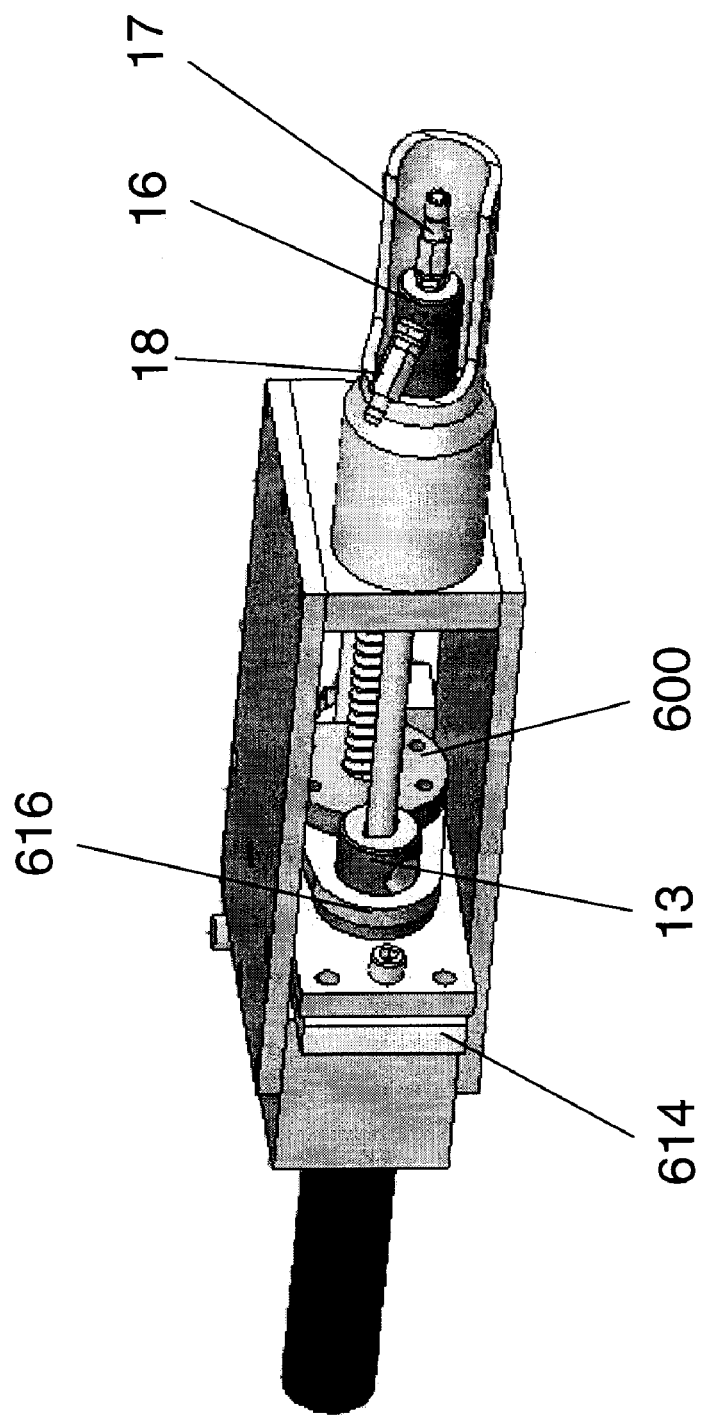
FIG. 11 is a perspective side view of the needle-free injection device of FIG. 7, showing the charging mechanism in the rearward position.
Figure 12:
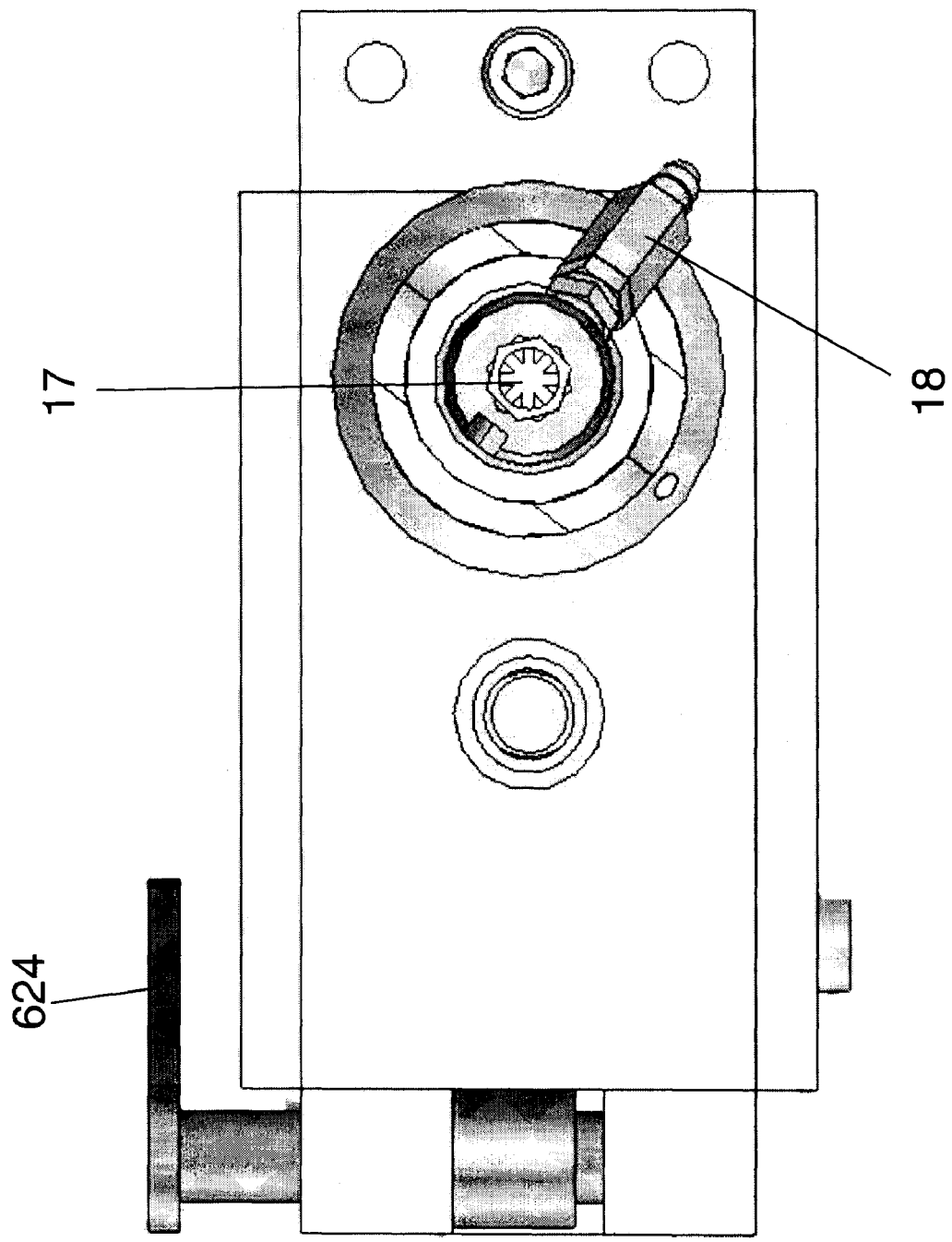
FIG. 12 is a front view of the needle-free injection device of FIG. 7, showing the charging mechanism in the rearward position.
Figure 13:
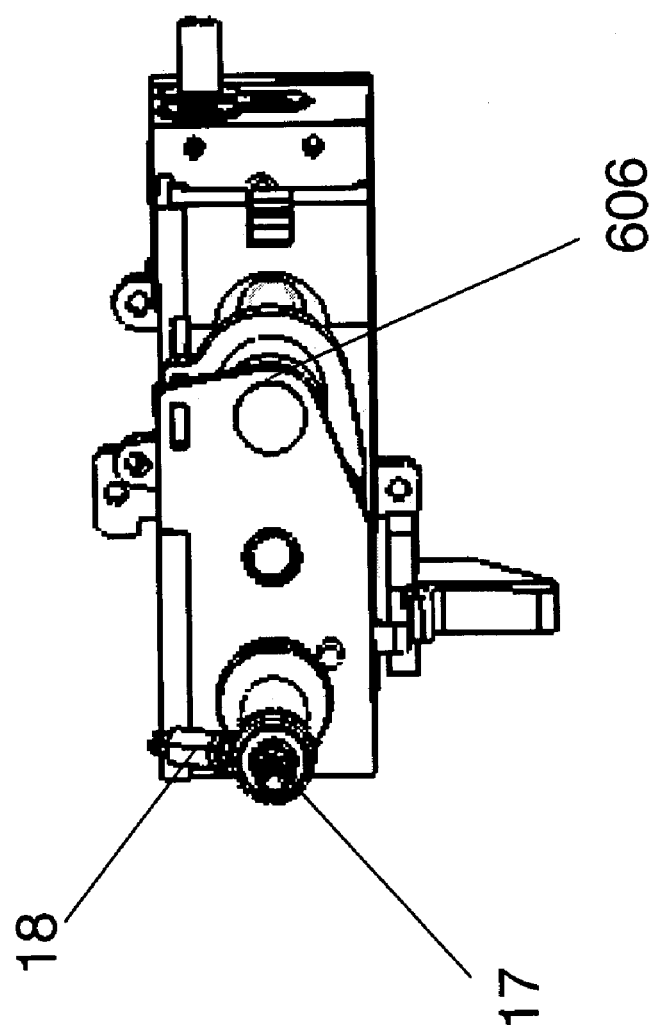
FIG. 13 is a front view of the needle-free injection device according to one embodiment of the present invention.
Figure 14:
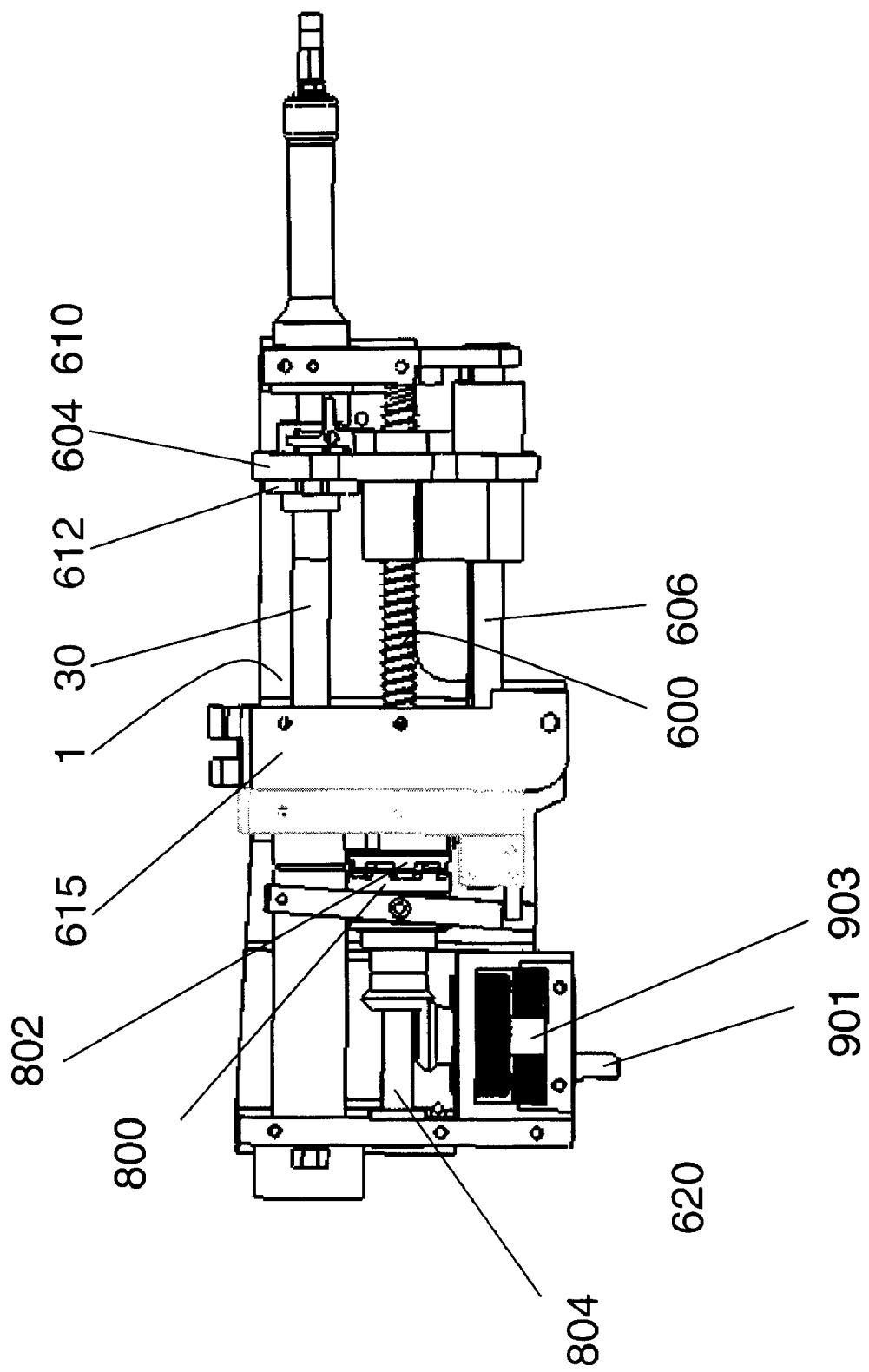
FIG. 14 is a side view of a needle-free injection device according to one embodiment of the present invention, showing the charging mechanism in the forward position.
Figure 15:
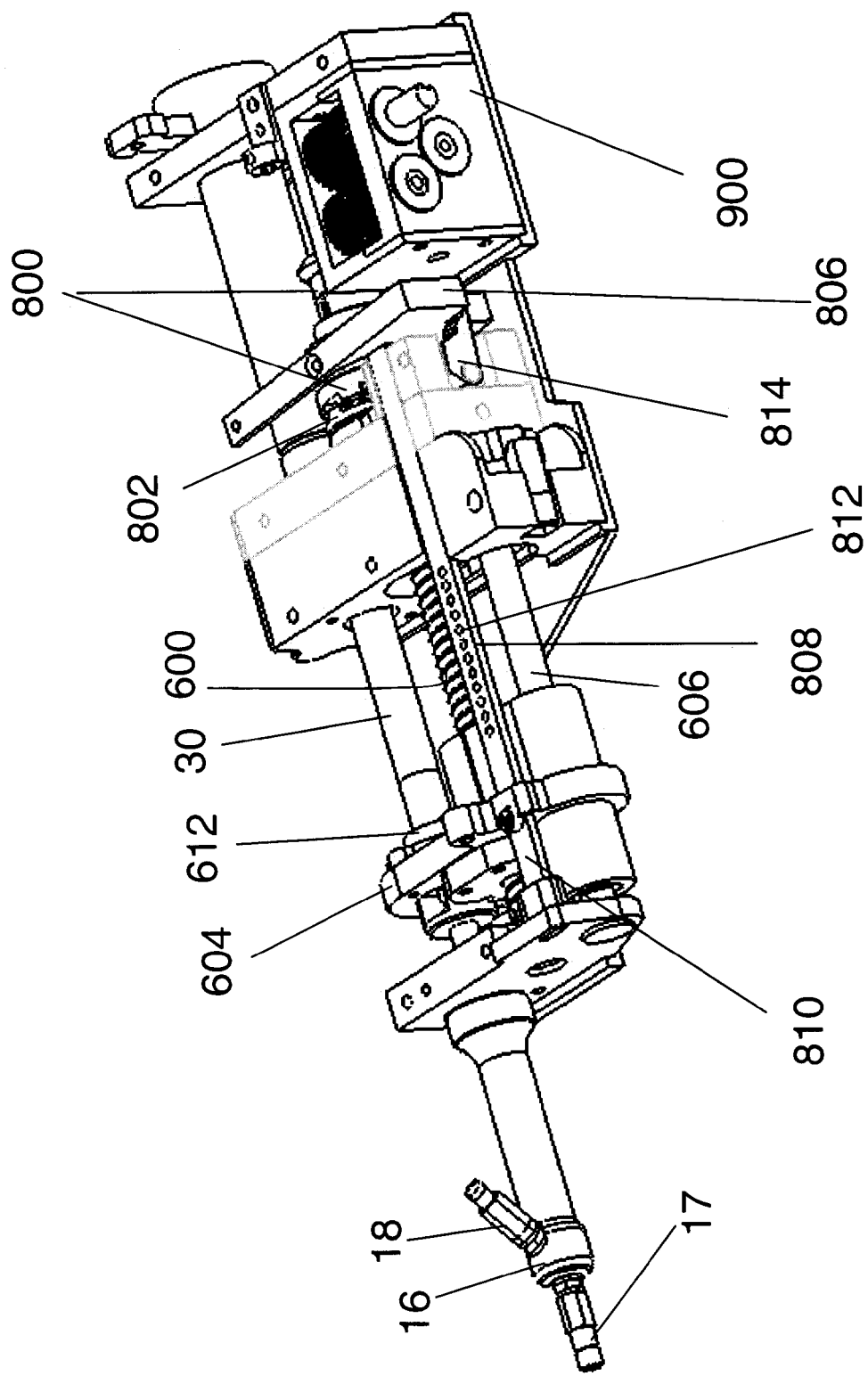
FIG. 15 is a perspective side view of the needle-free injection device of FIG. 14.
Figure 16:
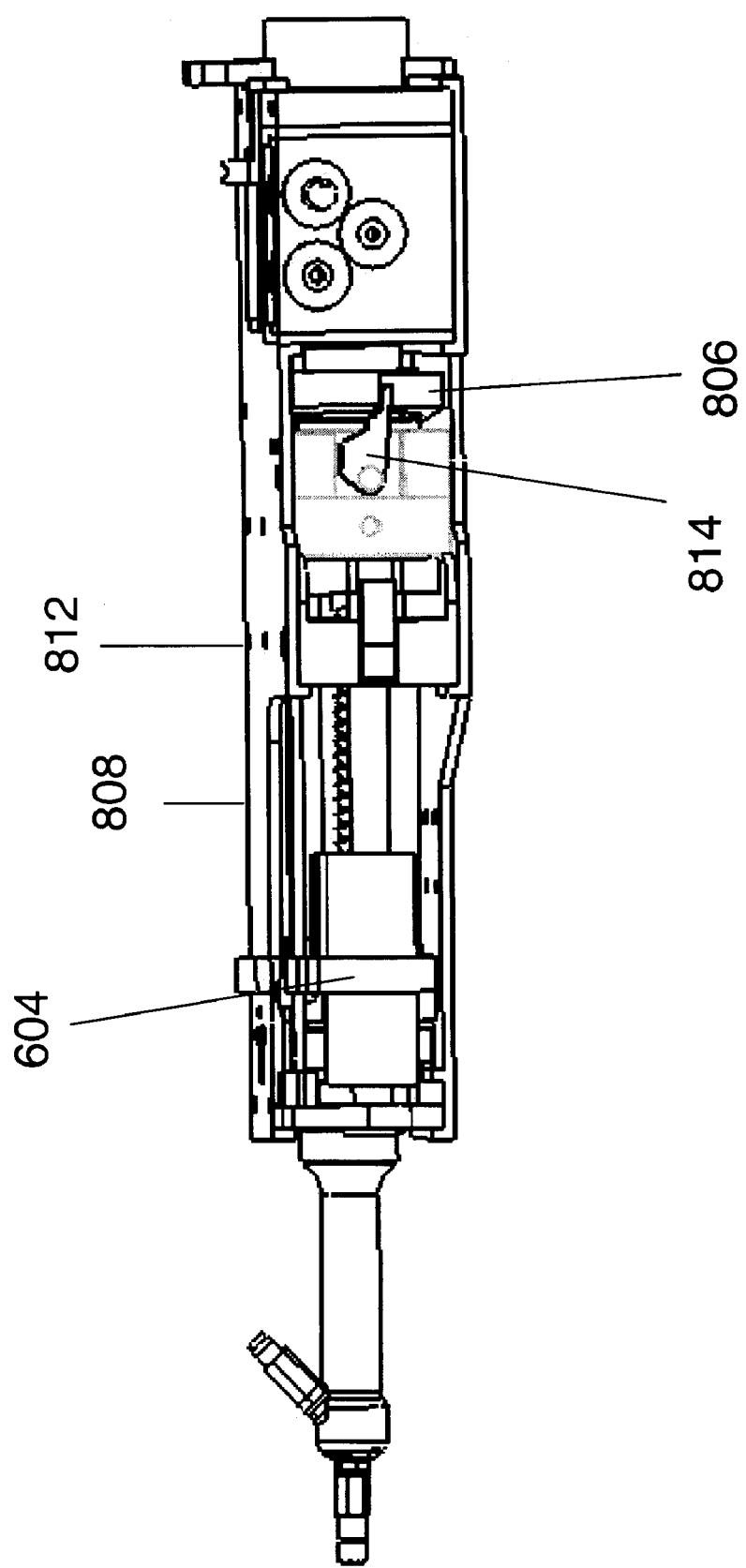
FIG. 16 is a side view of the needle-free injection device of FIG. 14.
Figure 17:
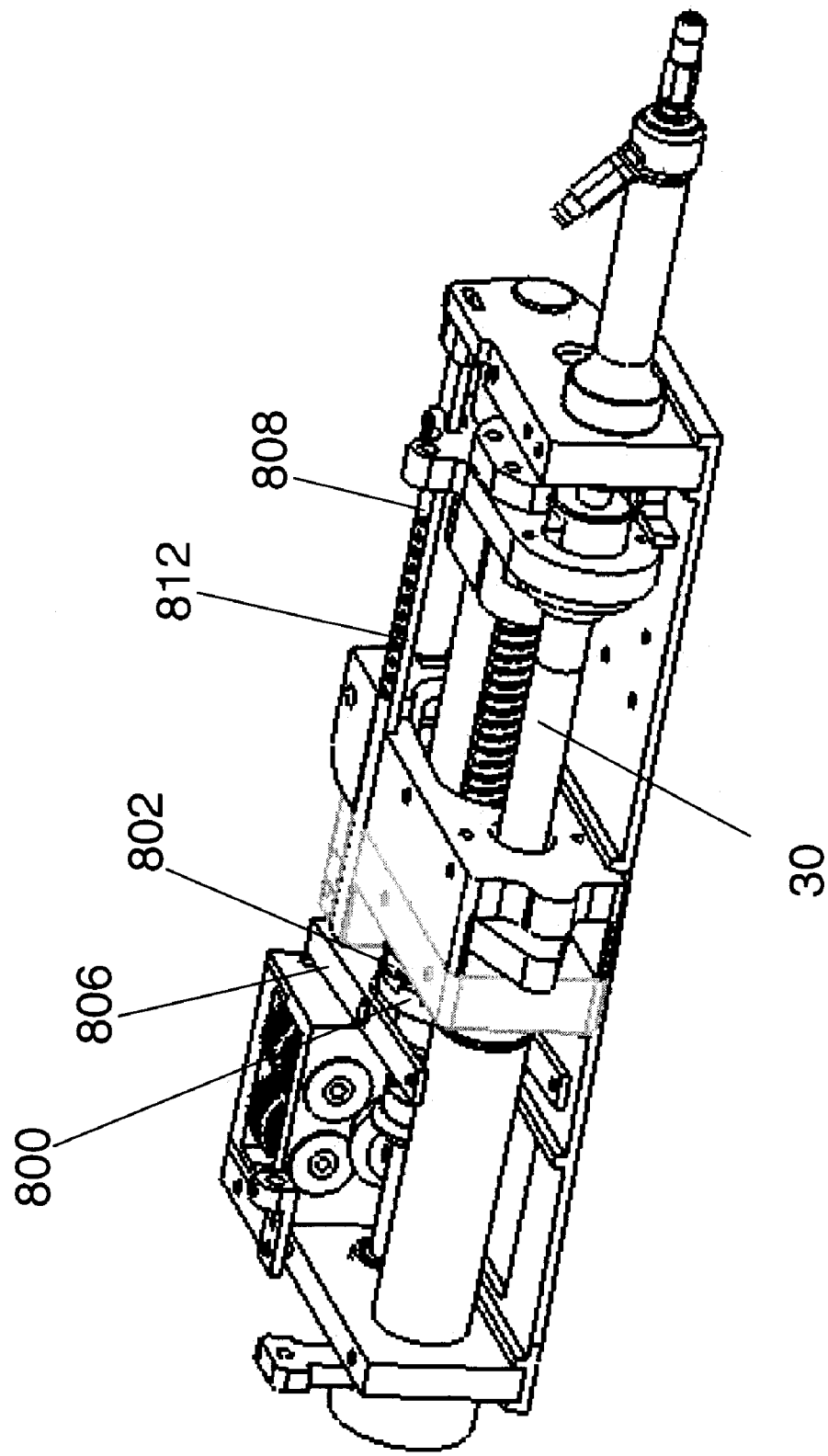
FIG. 17 is a perspective side view of the needle-free injection device of FIG. 14.
Figure 18:
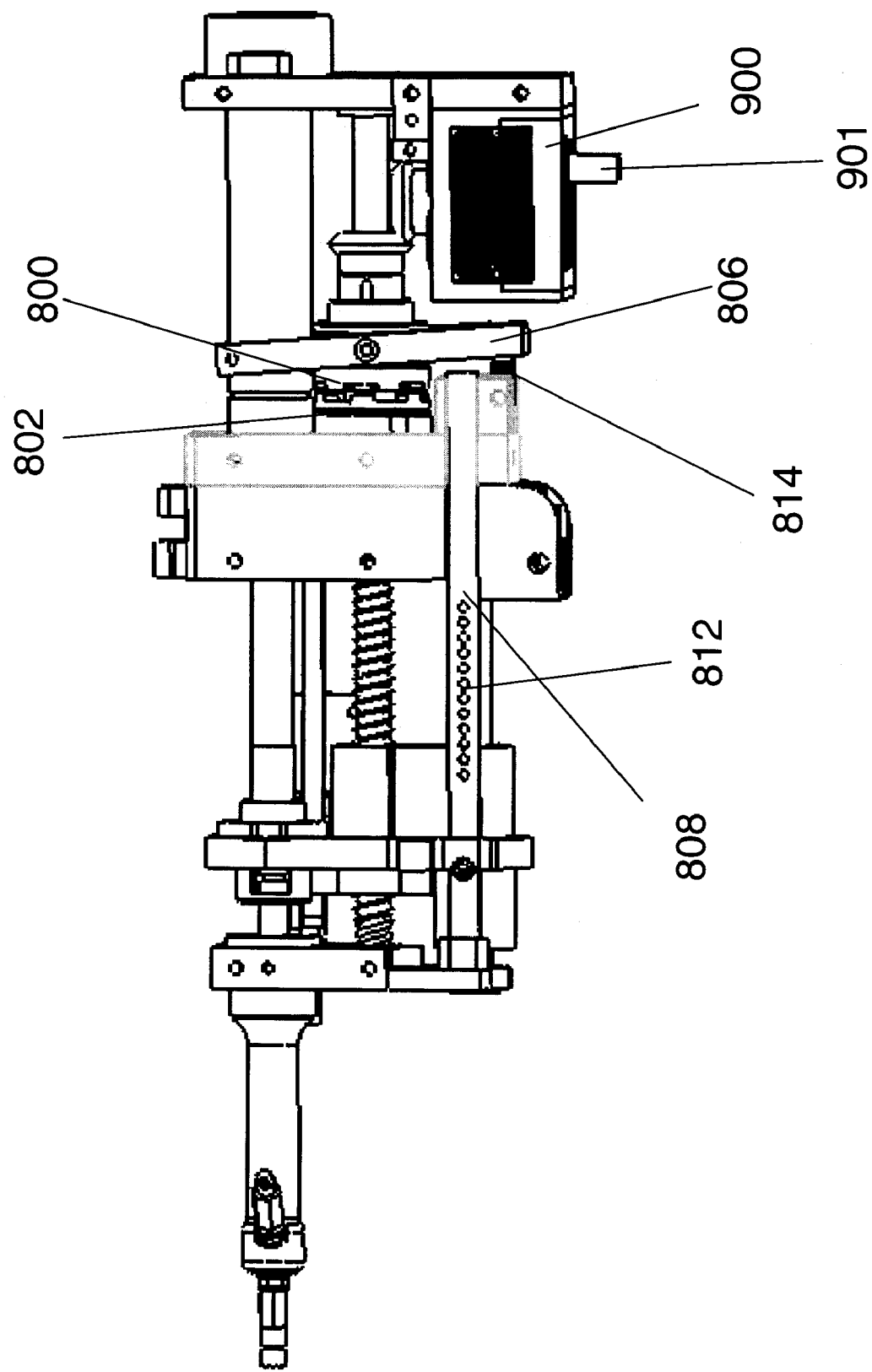
FIG. 18 is a top view of the needle-free injection device of FIG. 14.
Figure 19:
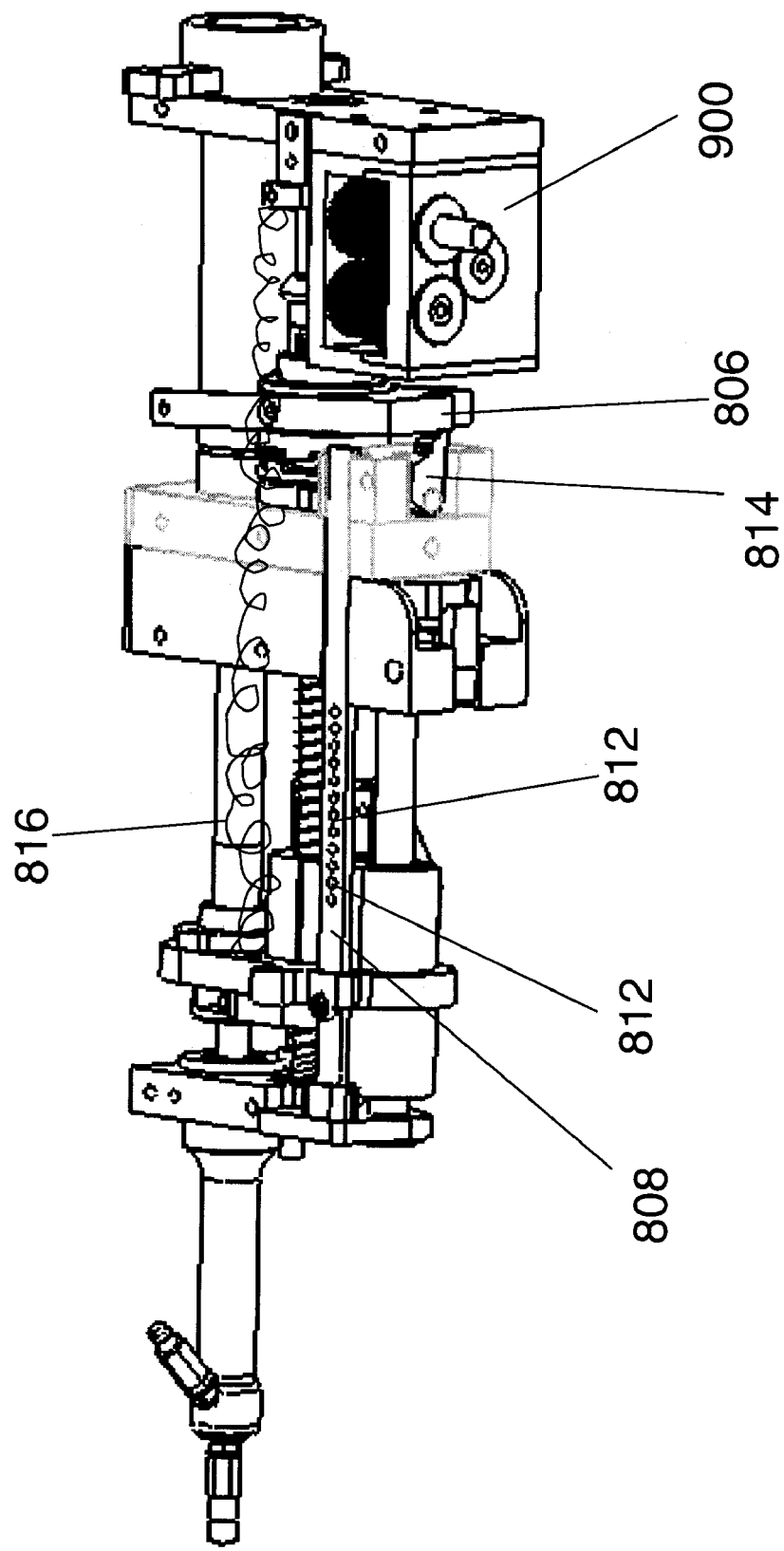
FIG. 19 is a perspective side view of the needle-free injection device of FIG. 14.
Figure 20:
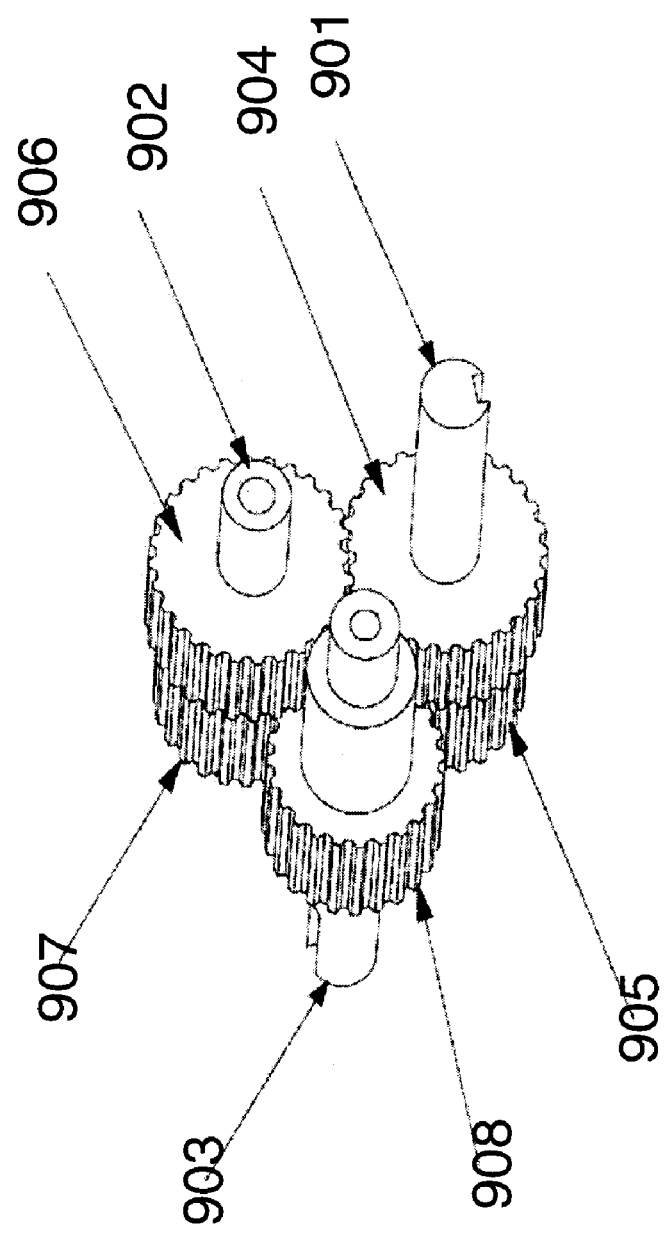
FIG. 20 is a perspective side view of one embodiment of the two-way drive transmission of the present invention.
Figure 21:
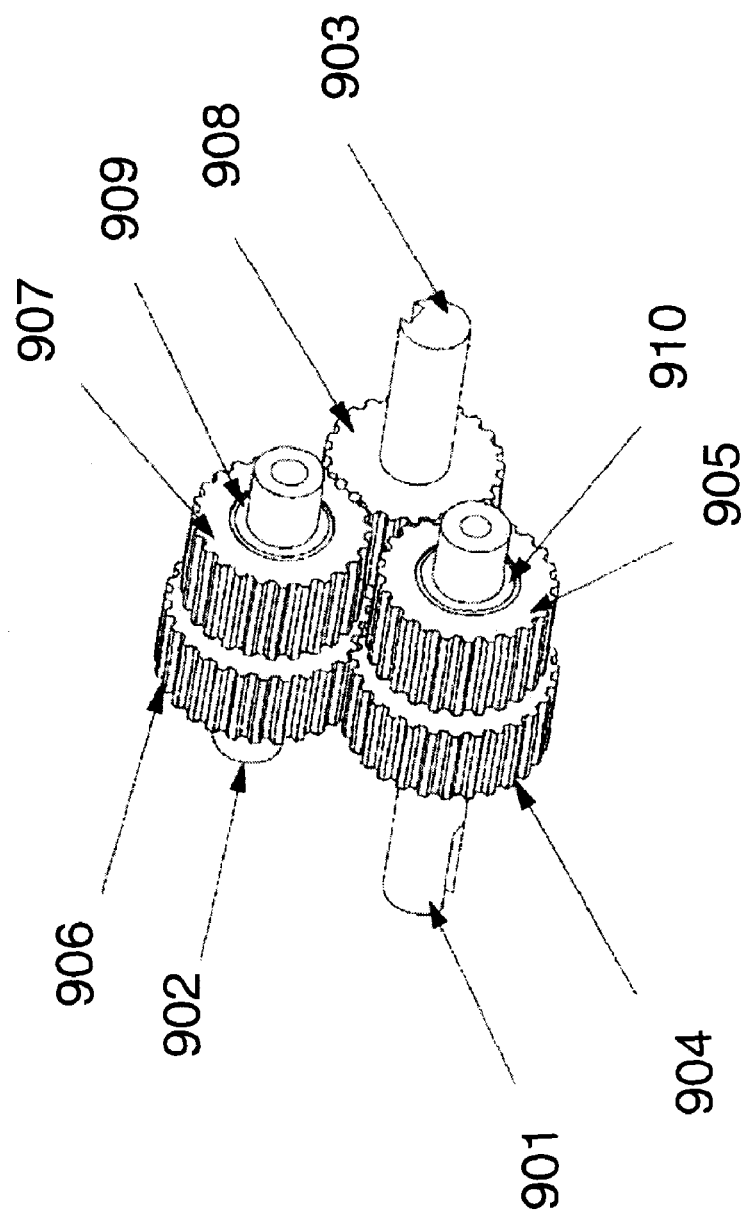
FIG. 21 is a perspective side view of the two-way drive transmission of FIG. 20.
Figure 22:
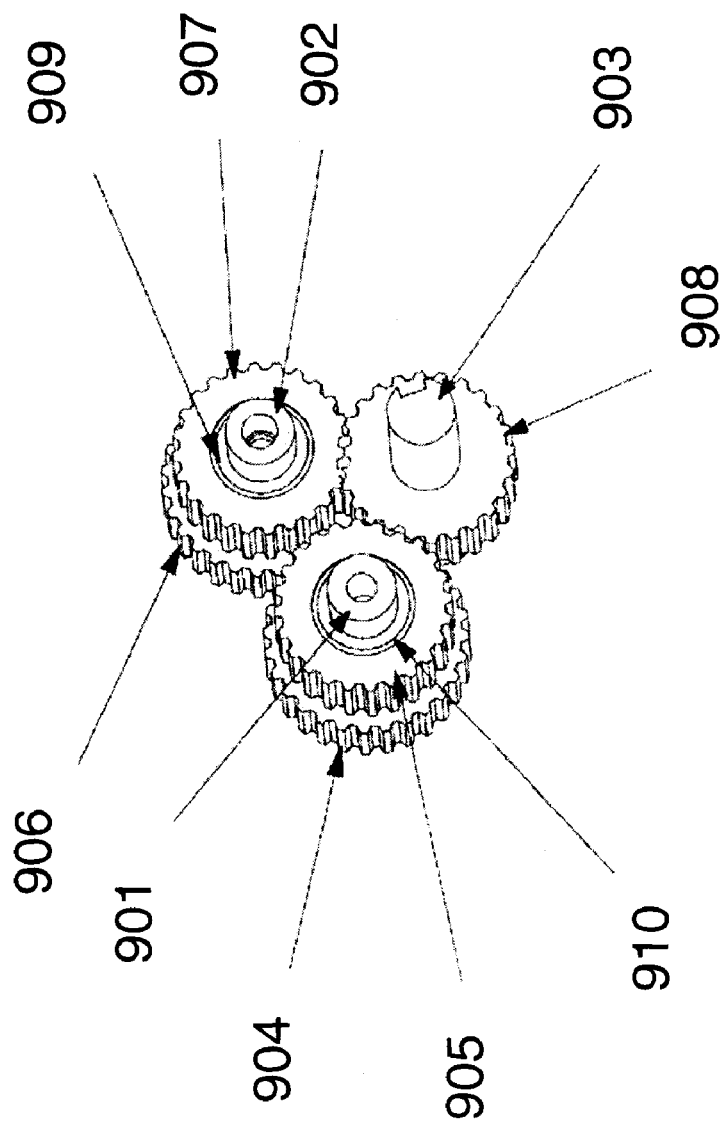
FIG. 22 is a perspective side view of the two-way drive transmission of FIG. 20.
Figure 23:
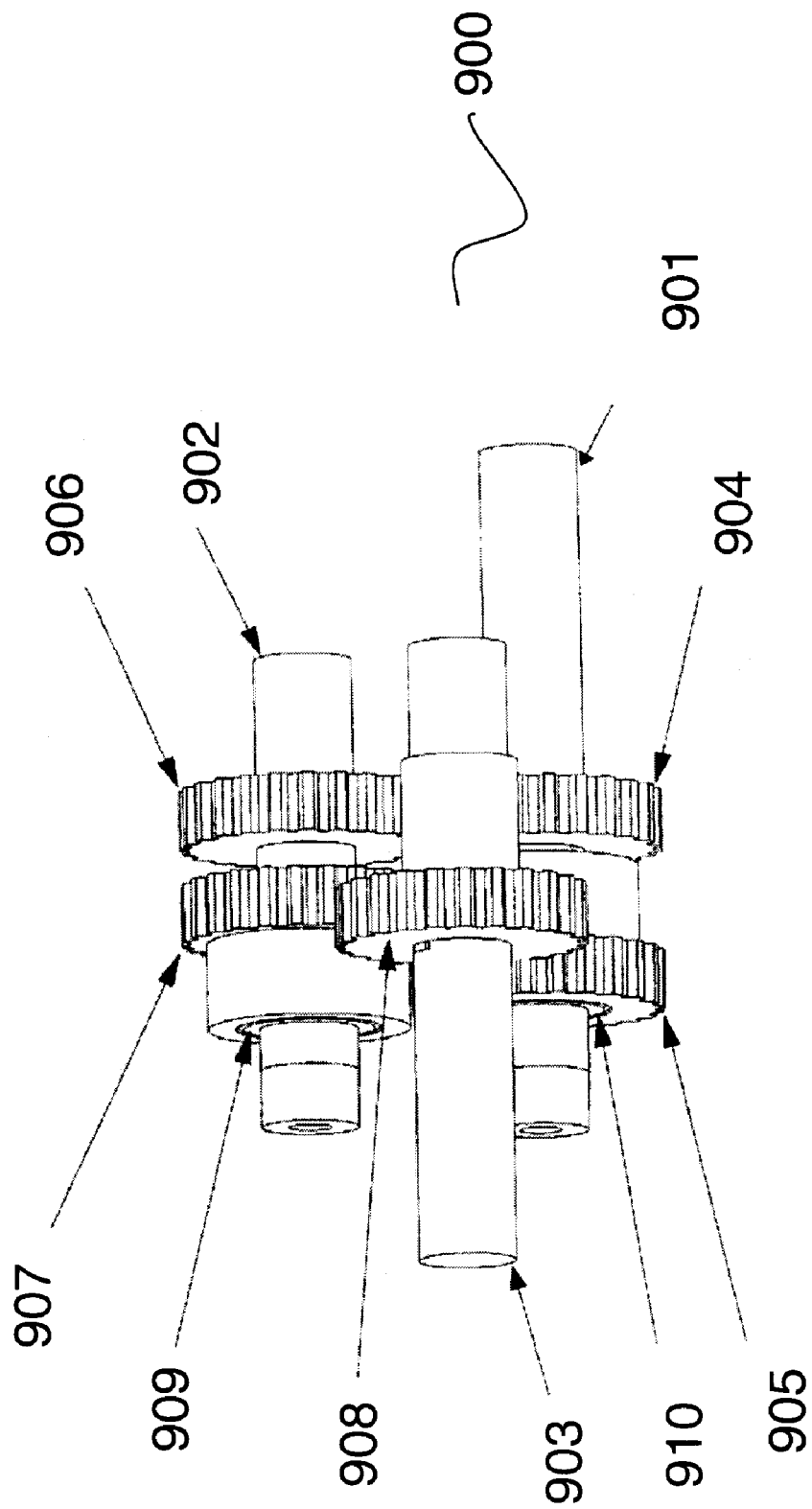
FIG. 23 is a front view of the two-way drive transmission of FIG. 20.
Figure 24:
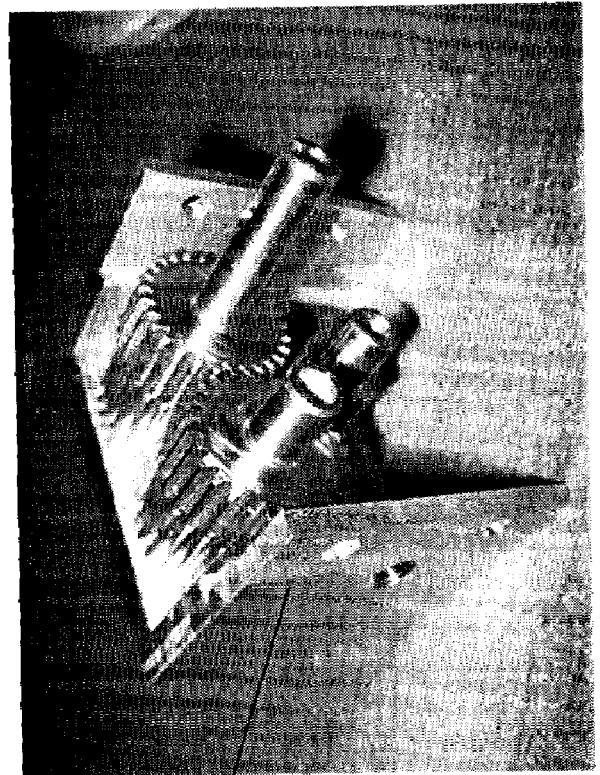
FIG. 24 is a perspective top side view of the two-way drive transmission of FIG. 20.
Figure 25:
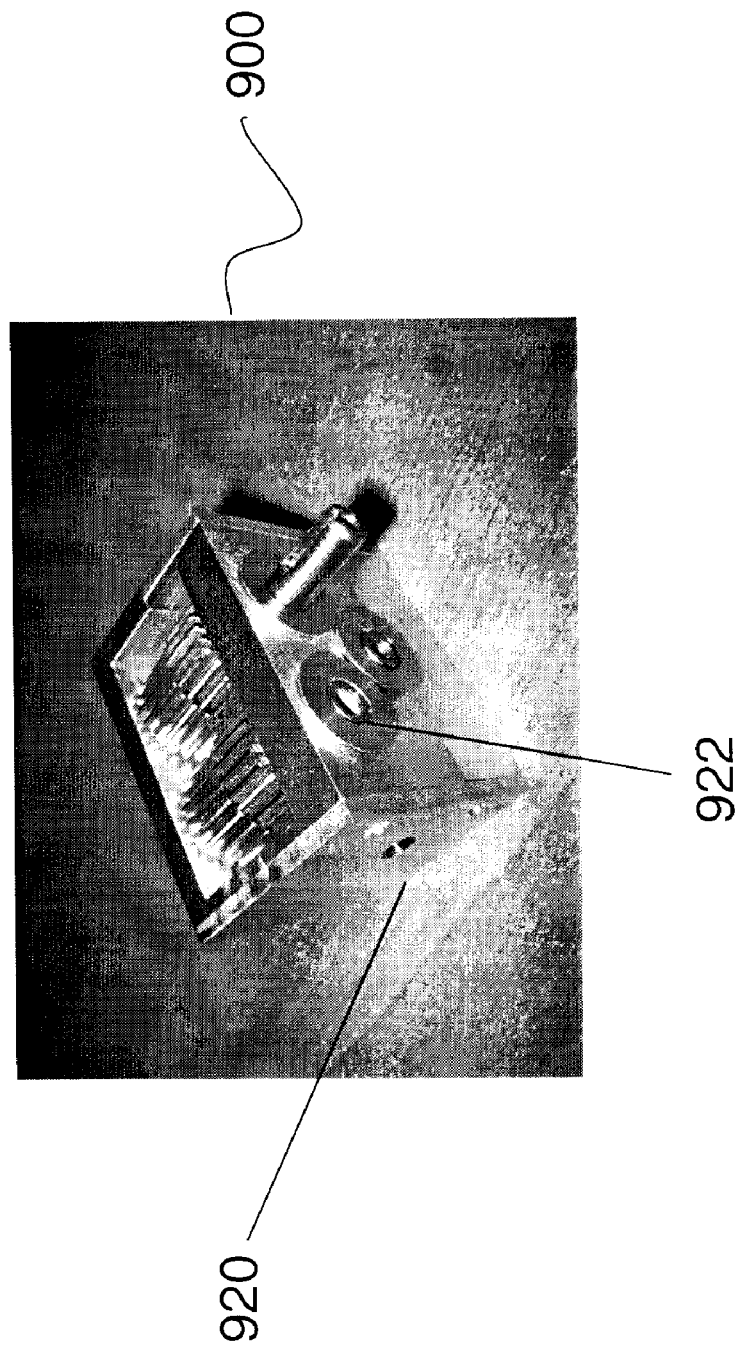
FIG. 25 is a perspective top side view of the two-way drive transmission of FIG. 20.
Figure 26:
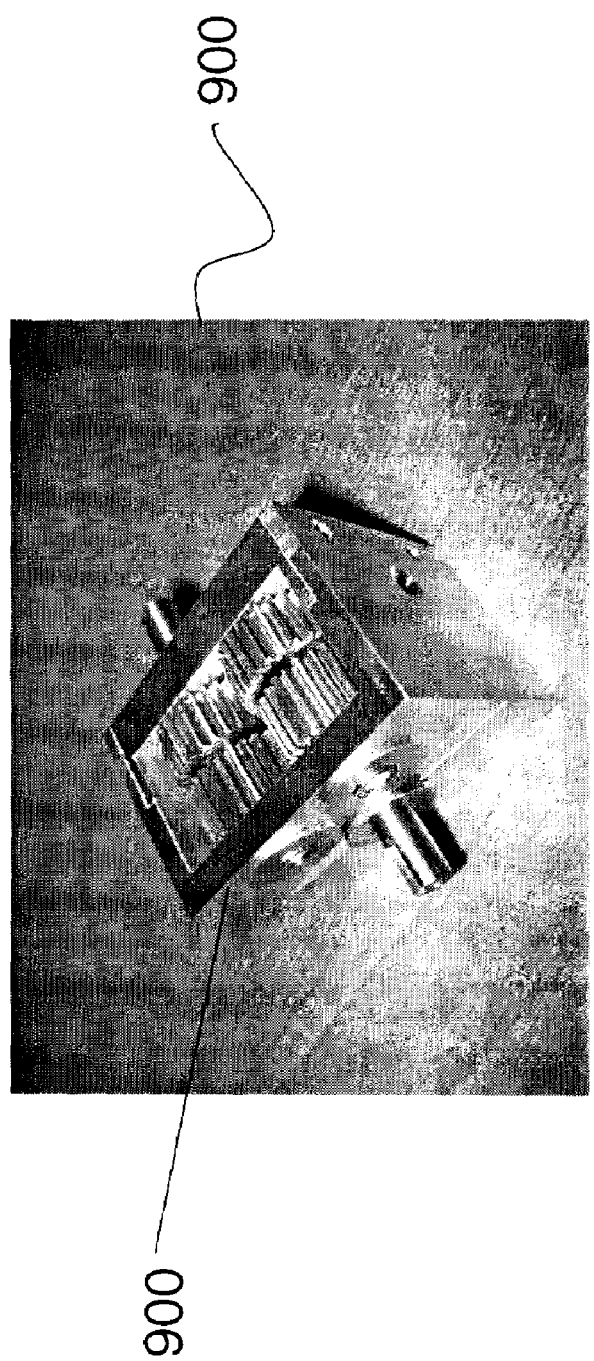
FIG. 26 is a perspective top side view of the two-way drive transmission of FIG. 20.

The appropriate gap-distance X is selected to maximize the velocity of piston and rod assembly 32 following triggering of the device and before direct or indirect impact with plunger 15. This, in turn, maximizes the available force for impact of the liquid at the orifice end of the device. This impact force is important to the operation of the device, since it provides the opening for the medicament to pass through the skin and the subcutaneous tissue. Gap-distance X also allows the injector to perform injections in large animals using relatively low pressures because the impact required for piercing skin and subcutaneous tissue is far greater than the pressure required to inject the remaining dosage of the medicament into the desired tissue. This makes the injector safer and much less painful to the subject receiving an injection in comparison to conventional needle-free injection devices. To draw a comparison, when triggered, an injector that operates with one constant pressure during an injection pierces the skin and subcutaneous tissue and delivers the liquid to be injected using the same pressure. If the user moves or slides the orfice end of the device during this process the flesh of the subject can be sliced, as with a scalpel, thus potentially causing severe wounds. By including a gap-coupling 13, the pressure is delivered in a spike formation where, at impact, the pressure spikes to the desired level to pierce the tissue, but drops to perform the remainder of the injection (See FIG. 6).

If gap-distance X is too small, piston and rod assembly 32 is unable to reach maximum velocity, the impact is lessened and the force at the orifice available for piercing is less. If the gap-distance X is increased, very little effect on impact pressure results due to the fact that the maximum velocity has already been reached and therefore maximum force had been reached at the orifice end.

In one embodiment of the present invention, gap-distance X is a fixed distance. In one example the gap-distance is ⅜ inch. In an alternative embodiment, the gap-coupling is user adjustable such that the gap-distance can be varied depending on the application of the device. In another alternative embodiment, the gap-coupling is integral to rod 30.

In operation, as piston and rod assembly 32 moves from the rearward position to the forward position it travels gap-distance X before the impact end of rod 30 impacts, either directly (FIGS. 2 and 4) or indirectly, via transferring means 100 (FIGS. 4 and 5), the rear end of plunger 15. Plunger 15, in turn, moves from its rearward position to its forward position within dosing reservoir 16 so as to expel a liquid from dosing reservoir 16 through nozzle 17.

In accordance with a specific embodiment of the invention, plunger 15 is disposed within dosing reservoir 16 and is removably attached to gap-coupling 13. In one example, plunger 15 is attached to gap-coupling 13 by a threaded screw. In another example, plunger 15 is attached to gap-coupling 13 by a quarter-turn mechanism.

Charging Mechanism

Actuating device 40 of the needle-free injection device of the present invention further comprises a charging mechanism for moving piston and rod assembly 32, against the gas charge in gas tight chamber 4, from its forward to its rearward position. Through use of this charging mechanism, a user is able to "charge" the injection device in order to make it ready for injection. The charging mechanism can include manual or motorized means for moving piston and rod assembly 32.

In accordance with a specific embodiment of the present invention the means for moving piston and rod assembly 32 are motorized means. Such motorized means may include DC (optionally rechargeable) and/or AC power supplies. In one example, the motor will be removably mounted on its own assembly or within a bracket.

In accordance with an alternative embodiment of the present invention the means for moving piston and rod assembly 32 are manual means.

FIGS. 7-19 depict a needle-free injector according to one aspect of the present invention in which the charging mechanism comprises a threaded member/nut mechanism to transfer and/or amplify an actuation force applied to the injector for moving the piston and rod assembly against the gas charge. The threaded member/nut mechanism is operatively associated with either a manual means or motorized means for moving the piston and rod assembly in order to charge the actuator. The term "threaded member/nut mechanism" is used herein to refer to a combination of a threaded shaft engaged with a nut having an internal thread formed on an interior surface for threadingly engaging the threaded shaft. It should be understood that the shape and size of the nut member will vary depending on various parameters, including size of overall device, cost, materials, etc.

Referring to FIGS. 7-19, chamber 16 and nozzle 17 are disposed on first end 230 of housing 1 and actuating device 40 is disposed within block member 620 of housing 1. As described above, movement of the piston and rod assembly from its forward position to its rearward position charges actuation device 40. In the device depicted in FIGS. 7-19, charging of the injector is achieved by movement of the nut member along a length of the threaded shaft (via rotation of the threaded shaft) from a forward position to a rearward position, which in turn moves gap-coupling 13 and the piston and rod assembly from its forward to its rearward position.

In a specific embodiment, the threaded member/nut mechanism comprises a lead screw and a ball nut, and ball nut 602 is threadingly engaged on lead screw 600. Lead screw 600 further includes a ball bearings run in the larger threaded portion of lead screw. The following description refers to lead screw 600 and ball nut 602, however, this description is intended to provide an exemplary embodiment of the present invention and is not intended to limit the invention to the use of a lead screw and a ball nut.

In accordance with a specific embodiment of the present invention, the means for rotating lead screw 600 are motorized means. Such motorized means may include DC (optionally rechargeable) and/or AC power supplies. In one example, the motor will be removably mounted on its own assembly or within a bracket. In a specific embodiment, gearing, such as spur gears, are used to operatively connect the motorized means and the lead screw to achieved the desired speed and force control.

In accordance with an alternative embodiment of the present invention, the means for moving the piston and rod assembly are manual means. In one example, manual means include a hand crank. In a specific embodiment, the manual means includes an auto-reversing clutch system that mechanically senses the resistance of a dead stop, to reverse the rotation. This type of reversing mechanism is commonly used in automatic thread tapping tools, and would be well known to the skilled worker.

Commercial sources of ball nuts and lead screws suitable for use in this invention include, for example, NGK, WM Berg, and/or SKF. Such sources also sell variations of similar lead screws and ball nuts.

Lead screw 600 is operable for rotation, which in turn causes ball nut 602 to rotate and move between a forward position (FIG. 7) and rearward position (FIG. 8-12), as determined by the direction of rotation of lead screw 600. The ball nut is directly or indirectly connected to the gap coupling. In the specific example shown, plate member 604 connects ball nut 602 to gap-coupling 13. Plate member 604 includes a first guide passage in sliding relation with guide 606, and a second passage sized for removable attachment to gap-coupling 13.

In this embodiment, gap-coupling 13 includes first end 608 sized to slidingly fit within second passage 610 of plate member 604, and second end 612 sized such that is does not fit within second passage 610.

Movement of ball nut 602 from a forward position to a rearward position, and the corresponding movement of plate member 604, causes second passage 610 in plate member 604 to pass over first end 608 of gap-coupling 13 and abut second end 612, thereby engaging gap-coupling 13. In turn, the movement of gap-coupling 13 causes movement of the piston and rod assembly, from its forward position to its rearward position. Second passage 610 is prevented from passing over gap-coupling 13 due to the relative size of second end 612 of gap-coupling 13 compared to second passage 610 of plate member 604.

Charging of actuating device 40 continues until the desired charge is achieved. In one example, a dosage ring (not shown) is used to set the desired charge. In one example, the dosage ring is adjustable over a range of volumes between about 0.01 cc to about 5 cc.

FIGS. 13-19 depict a needle-free injector according to one aspect of the present invention in which the charging mechanism comprises a threaded member/nut mechanism to transfer and/or amplify an actuation force applied to the injector for moving the piston and rod assembly against the gas charge. In this example, the injector further comprises a two-way drive transmission as a rotation means to rotate lead screw 600 in order to charge actuation device 40. The two-way drive transmission can be functionally connected to the threaded shaft (e.g., lead screw) via a gear assembly or other means for translating input force to rotate the threaded shaft and thereby charge the injector.

In the specific example shown in FIGS. 13-19, a connecting gear assembly includes main drive gear 800, driven by two-way drive transmission 900 that is operatively associated with lead screw drive gear 802, and configured to rotate lead screw 600.

In this example, lead screw 600 engages lead screw drive gear 802. In one example, lead screw gear drive is removably attached to lead screw 600. In another example, lead screw drive gear is fixedly attached to lead screw 600.

Main shaft 804 has a first end attached to housing 1 and second end proximal to lead screw drive 802.

Main drive gear 800 includes a first end adapted for gearing fit with lead screw drive gear 802, a second end adapted for gearing fit with output shaft 901 of two way drive transmission 900, a saddle receiving portion between the first and second end, and a central passage such that main drive gear 800 is slidably mounted on main shaft 804.

Main gear saddle 806 includes a first end pivotably attached to housing 1, and a passage through which the saddle receiving portion of main drive gear 800 extends. The first and second ends of main drive gear 800 are configured such that they can not pass through the passage of main gear saddle 806 and each is positioned on opposite sides of main gear saddle 806. Thus, main drive gear 800 moves with main gear saddle 806.

A spring (not shown) urges the second end of main gear saddle 806 from a rearward position to a forward position, and in turn moves main drive gear 800 from a forward position to a rearward position. In the forward position, the first end of main drive gear 800 is brought into gearing contact with lead screw drive gear 800 and the second end of main drive gear 800 is in gearing contact with the output of shaft 901 of two way drive transmission 900. In the rearward position, main drive gear 800 is brought out of contact with lead screw drive gear 802 by movement of main gear saddle 806.

As noted above, charging of actuating device 40 continues until the desired charge is achieved. In one example, as seen in FIGS. 13-19, a dosage metering rod 808 comprising a plurality of dosage metering holes 812 and a dosage set point member (not shown) are used to set the desired charge. A user and/or a manufacturer adjusts the dosage set point member on dosage metering rod 808 to a position that will provide the desired charge. Optionally, dosage metering rod 808 includes marking or indicia to identify the charge and/or dosage of a respective setting.

Dosage metering rod 808 is slidably mounted within housing 1 and a passage in plate member 604, and includes a first end and a second end. The first end of dosage metering rod 808 is sized for sliding fit through a passage in plate 604, and also includes a dosage pin (not shown, but generally indicated by 810) at a position distal to plate member 604. The dosage pin is sized such that it does not fit through the passage in plate member 604.

Dosage metering rod 808 is moveable from a forward position to a rearward position. In the forward position, the second end is out of contact with main gear saddle 806; in the rearward position, the second end is brought into contact with main gear saddle 806 and moves saddle gear from its forward position to rearward position. Thus, when dosage metering rod is moved to the rearward position, main drive gear 802 is brought out of contact with lead screw drive gear 802.

In use, a dosage set point member (not shown) is removably or fixedly placed in at least one dosage adjustment hole 812. As charging of actuating device 40 occurs, plate member 604 moves from the forward position to the rearward position. Dosage metering rod 808 is slidingly disposed within the passage of plate member 604 and so slides along dosage metering rod 808. As plate member 604 abuts the dosage set point member positioned within dosage metering holes 812, dosage metering rod 808 is moved from the forward position to the rearward position. As noted above, when dosage metering rod 808 is moved to the rearward position, the second end of dosage metering rod 808 moves main gear saddle 806 to the rearward position and therefore moves main gear drive 800 to the rearward position. When main gear saddle 806 is moved to its rearward position, main gear drive 800 is moved to its rearward position and moved out of contact with lead screw drive gear 802, thereby stopping movement of lead screw 600.

Once main gear saddle is moved to the rearward position, a spring (not shown) urges lock out pawl 812 from a first to a second position. In the second position, lock out pawl 812 maintains main gear saddle 806 in the rearward position.

Thus, charging of actuation device occurs until set point feature on metering rod 808 is encountered. Positioning of the dosage set point member in at least one dosage metering hole 812 along the length of the dosage metering rod 808 sets the charge of the actuation device 40. In one example, dosage metering rod 808 is adjustable over a range of volumes, for example, volumes between about 0.01 cc to about 5 cc.

Referring to FIGS. 7-26, in one example, means for rotating lead screw 600 further comprise a two-way drive transmission 900. In this example, two-way drive transmission 900 is fixedly or removeable attached to housing 1. Two-way drive transmission 900 comprises an input that is operatively associated with manual or motorized means for operating the input, and an output is operatively associated with the lead screw.

Two-way drive transmission 900 comprises input shaft 901, idler shaft 902 and output shaft 903. Shafts 901, 902 and 903 are mounted in a frame or housing 920 and are supported by bearings 922 for rotation about their longitudinal axis Input shaft 901 carries gear 904 and gear 905. Gear 904 is fixedly mounted on input shaft 901 by locking key or other suitable means for rotation in the same direction as input shaft 901. Gear 905 is mounted on unidirectional clutch bearing 910 which is configured for (i) free rolling when input 901 is rotated in the counterclockwise direction and (ii) locking on shaft 901 when input shaft 901 is rotated in the clockwise rotation. Unidirectional clutches and/or bearings may be made from a variety of materials, and can be obtained from suppliers such as Timkem, WM Berg and McMaster Carr.

Idler shaft 902 carries gear 906 and gear 907. Gear 906 is fixedly mounted on idler shaft 902 by locking key or other suitable means for rotation in the same direction as idler shaft 902. Gear 907 is mounted on unidirectional clutch bearing 909 and is configured for (i) free rolling when idler shaft 902 is rotated in the counterclockwise direction and (ii) locking on idler shaft 902 when rotated in the clockwise direction.

Output shaft 903 carries gear 908 which is fixedly mounted on output shaft 903 by locking key or other suitable means.

Gear 904 is in meshing engagement with gear 906. Gear 907 is in meshing engagement with gear 908. Gear 905 is in meshing engagement with gear 908. Gears 905 and 907 are longitudinally offset such that they each maintain partial facial engagement with gear 908 but are out of meshing engagement with one another.

Clockwise Rotation of Input Shaft 1

Clockwise rotation of shaft 901 locks unidirectional clutch bearing 910 and causes clockwise rotation of gear 905, which, in turn, causes counterclockwise rotation of gear 908 and output shaft 903.

Clockwise rotation of shaft 901 causes clockwise rotation of gear 904, which, in turn, causes counterclockwise rotation of gear 906 and idler shaft 902. As idler shaft 902 rotates freely in the counterclockwise direction within unidirectional clutch bearing 909 this rotation does not drive gear 907. As gear 907 is in meshing engagement with gear 908, the counterclockwise rotation of gear 908 will cause clockwise rotation of gear 907 which is permitted to free-wheel on idler shaft 902 by the operation of clutch bearing 909.

Counterclockwise Rotation of Input Shaft 1

Counterclockwise rotation of shaft 901 causes counterclockwise rotation of gear 904 which causes clockwise rotation of gear 906 and idler shaft 902. Clockwise rotation of idler shaft 902 locks unidirectional clutch bearing 909 and causes clockwise rotation of gear 907 which, in turn, causes counterclockwise rotation of gear 908 and output shaft 3

As input shaft 901 rotates freely in the counterclockwise direction within clutch bearing 910, this rotation does not drive gear 905. As gear 908 is in meshing engagement with gear 905, the counterclockwise rotation of gear 908 will cause clockwise rotation of gear 905 which is permitted to freewheel on input shaft 901 by the operation of clutch bearing 910.

In this example, both clockwise and counterclockwise rotation of input shaft 901 causes counterclockwise rotation of output shaft 903. It will be appreciated that operation of the two way drive transmission can be changed such that clockwise and counterclockwise rotation of input shaft 901 causes clockwise rotation of output shaft 903. For example, the direction of unidirectional clutch bearing 909 and unidirectional clutch bearing 910 can be reversed.

Two-way drive transmission 900 may be a variety of sizes and can be made from a variety of materials, as may be determined by user preferences, material cost and availability, intended uses, and/or the like. Suitable materials, include but are not limited to simple regular polycarbonate plastic, nylon, glass filled nylon, Teflon, aluminum, steels of various hardness, and stainless steel.

Manual means or motorized means can be used to rotate input shaft 901. Motorized means may include DC (optionally rechargeable) and/or AC power supplies. In one example, the motor will be removably mounted on its own assembly or within a bracket.

In accordance with a specific embodiment of the present invention, the means for rotating input shaft 901 are manual means, such as a hand crank. A handle operable by a user is moved in a back and forth, or up and down, motion, acting on input shaft 901. Although the user may provide opposite directions of input, the transmission converts this to a single direction of output.

In the case in which a two way drive transmission is incorporated into a needle-free injector, a handle operable by a user is moved in a back and forth, or up and down, motion, acting on input shaft 901. Although the user may provide opposite directions of input, the transmission converts this to a single direction of output, and operation of the lead screw.

Alternatively, motorized means may be used to rotate input shaft 901.

It will be clear that the two way drive transmission may be fixedly or removably incorporate into the needle free injector. The two way drive transmission may be used in a kit to replace needle-free injectors that already include such a two way drive transmission, e.g., a replacement part. Alternatively, the two way drive transmission may be used to retrofit existing needle free injectors, to incorporated such a two way drive transmission.

In accordance with a specific embodiment, the device includes a visual signal and/or an audible signal to indicate to a user that the actuator is charged. In an alternate embodiment, a visual signal and/or an audible signal indicates that the actuator is charged, the trigger engaged, the nut 602 has returned to its forward position and the device is ready to be fired.

Trigger

Once in the rearward position, piston and rod assembly 32 is held in place by a trigger. The trigger is a mechanism that maintains piston and rod assembly 32 in the rearward position and is user activatable to allow piston and rod assembly 32 to be released from its rearward position to move to the forward position due to the pressure generated by the compressed gas-charge.

In contrast to the injection device of the present invention, previous injectors required that the trigger be depressed during the entire course of the injection. In such injectors, if the user stops depressing the trigger, the injection process ceases. Therefore, these prior devices can result in incomplete administration of the desired dose of the medicament due to user error in using the trigger.

In accordance with one embodiment of the present invention, the injection device includes a trigger guard, which is designed to minimize or eliminate the possibility of unintentional triggering of the actuated device.

In the specific embodiment depicted in the FIGS. 7-19, the trigger mechanism comprises trigger plate 614. Trigger plate 614 includes a locking passage (not shown), which is adapted for sliding fit over rod 30. Trigger plate 614 is movable between a locked and unlocked position. In the unlocked position, the locking passage is generally aligned with rod 30, and rod 30 is in sliding relation with the locking passage. In the locked position, the trigger plate 614 is moved such that the locking passage is generally out of alignment and the inner walls of the locking passage engage rod 30. Thus, in the locked position, trigger plate 614 frictionally engages rod 30 so as to maintain rod 30 of the piston and rod assembly in place.

In one example, trigger plate 614 is kept in general alignment with rod 30 (and thus maintained in the unlocked position) using simple springs located between trigger plate 614 and back block 620.

Thus, during charging, trigger plate 614 is acted on by a spring (not shown) which maintains locking passage generally aligned with rod 30, and rod 30 is free for sliding relation with locking passage. When charging is complete, or the direction of rotation of the lead screw is reversed, piston and rod assembly 32 is urged to the forward position and the spring then pushes trigger plate 614 to the locked position. Trigger plate 614 is prevented from forward movement because block member 615 holds it back. Block member 615 is secured in place on either side by the frame plates of housing 1.

In accordance with a specific embodiment, trigger plate 614 is attached to cam 622, which is attached to lever 624. Rotation of lever 624 causes movement of cam 622, which moves trigger plate 614 from the locked position to the unlocked position, and the piston and rod assembly is freed for movement to the forward position.

Once trigger plate 614 is disengaged from rod 30, forward movement of the piston and rod assembly is committed, that is, there is nothing to stop or slow movement of the piston and rod assembly from its rearward to its forward position in response to the compressed gas-charge. In the case of the device comprising a remote portion and a hand-held portion, user activation of the trigger may be effected on either a remote portion or hand-held portion or both.

In one example, barrel trigger 700 is operatively associated with trigger plate 614. In this example, nozzle 17 is pushed onto the body to be injected with enough force to move barrel trigger 700 against a barrel spring so as to move trigger plate 614 from its locked to its unlocked position.

In another example, once the piston and rod assembly has returned to the forward position, an electrical switch (not shown) is activated, which allows motorized means to start and recharge the unit again.

In accordance with one embodiment of the present invention, the injection device includes a trigger lock, which is designed to minimize or eliminate the possibility of unintentional triggering of the actuated device.

In the specific examples shown in the Figures, when charging of the injection device is complete, or the direction of rotation of the threaded shaft is reversed, piston and rod assembly 32 is urged to the forward position and the spring then pushes trigger plate 614 to the locked position. Trigger plate 614 is prevented from forward movement because block member 615 holds it back.

Once main gear saddle 806 is brought out of contact with lead screw drive gear 800, trigger plate 614 is adapted for movement from the unlocked position to the locked position. Lead screw 600 is then free of any load and is also able to turn in both directions. The ball nut plate is urged forward by a mechanical spring 816 to the forward position ready for the next charging cycle.

As plate member 604 move to the forward position, the passage in plate member 604 moves along dosage metering rod 808. As plate member 604 abuts dosage pin 810, dosage metering rod is moved from the rearward to the forward position.

When the needle free injector is operated for the next injection, it resets the lock out pawl 814, moving pawl 814 from its second position to the first position, which allows gear saddle 806 to move forward, which allows main drive gear 800 to move to the forward position, and engage lead screw drive gear 806. The mechanism is now ready to be charged again.

It will be appreciated that the nut 602 must be moved from the rearward position to the forward position prior to activation. Returning nut 602 to the forward position is accomplished by rotating lead screw 600 in the direction to that which moved it to the rearward position.

Application and Use of Needle-free Injector

As would be readily appreciated by a worker skilled in the art, the positioning of the nozzle against the subject will depend on a number of factors, including, but not limited to, the species and body region to be injected, the age of the subject to be injected, and the pressure of the gas charge. For example, certain animal species will have skin that is more difficult to pierce than others. This is due, in part, to species differences in skin thickness. Additionally, members of a particular species will have regions of the body that are more or less difficult to inject. The age of the animal and or human may also have an effect on the ease of injection, since skin thickness and coarseness can vary with age. For example, in some species, a younger individual (e.g., neonate or infant) will have skin that is more readily injectable than an adult individual. As well, in a variety of animals, for example, regions behind the ears or in creases of limbs will typically be easier to inject. Those body regions that are more readily injected will require a lower pressure gas charge compared to a body region that is more difficult to inject. The skilled worker will appreciate and take into consideration the various species, body region and/or age differences, when selecting the pressure of the gas-charge.

The injection device of the present invention optionally includes a supply reservoir for supplying liquid to dosing reservoir 16. In a specific, non-limiting example, as depicted in FIGS. 1 and 5, supply reservoir is syringe 21 containing a medicament. In FIG. 4 the supply reservoir is bottle 208 containing a medicament. Syringe 21 and bottle 208 are connected to dosing reservoir 16 by a length of tubing 19 and a one-way valve 18. One-way valve 18 allows unidirectional movement of medicament from syringe 24 to dosing reservoir 16. In these embodiments movement of plunger 15 from the forward position to the rearward position in dosing reservoir 16 causes a single dose of medicament to be drawn from syringe 21 into dosing reservoir 16.

In accordance with another aspect of the present invention there is provided a method of using the needle-free injection device for injection of a liquid through the skin of a subject, that may be an animal or human. The method comprises the steps of (i) providing a needle-free injection device of the present invention having at least one dose of the liquid to be administered; (ii) actuating the device by moving piston and rod assembly 32 to the rearward position; placing nozzle 17 against the skin of the subject to be injected; and (iii) triggering the actuation device to expel a dose of the liquid through the outlet orifice and nozzle 17 and through the skin of the subject.

In accordance with another aspect of the present invention there is provided a kit for using the needle-free injector injection device of the present application.

In accordance with another aspect of the present invention there is provided a kit for adapting a needle-free injector for use with the charging mechanism of the present invention.

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A needle-free injection device for delivering a medicament under pressure from a dosing reservoir through an outlet orifice for administration to an animal or human, of the type comprising a plunger slidably received in said dosing reservoir and movable in a forward direction for expelling said medicament through said orifice, said injection device comprising an actuating device and said actuating device comprising:
   (a) a gas tight chamber;
   (b) a piston and rod assembly slidably received in said chamber and movable between a forward position and a rearward position;
   (c) a gas charge in said chamber for urging said piston and rod assembly to said forward position;
   (d) a charging mechanism for moving said piston and rod assembly against said gas charge into said rearward position, said charging mechanism comprising a threaded shaft threadingly engaged with nut member that is operatively associated with said piston and rod assembly and moveable along a length of the threaded shaft when said threaded shaft is rotated; and
   (e) a trigger for releasably retaining said piston and rod assembly in said rearward position,
   whereby activating said trigger causes said piston and rod assembly to be released for movement by said gas charge to said forward position so as to impact said plunger directly or indirectly with a force sufficient to cause said plunger to move in said forward direction to expel said medicament through said outlet and whereby said gas tight chamber is adapted to minimize or prevent the escape of said gas charge so as to maintain said gas charge is a pressurized state.

2. The needle-free injection device according to claim 1, wherein the circumference of the piston of said piston and rod assembly defines an outer edge that is in contact with the interior surface of said gas tight chamber such that the piston defines an extension portion and a compression portion of said gas tight chamber.

3. The needle-free injection device according to claim 2, wherein said piston of said piston and rod assembly comprises a passage for fluid communication between said extension portion and said compression portion of the gas tight chamber.

4. The needle-free injection device according to claim 1, wherein said gas charge is a compressed inert gas or a mixture of compressed inert gas.

5. The needle-free injection device according to claim 1 further comprising a lubrication medium for lubricating said piston and rod assembly.

6. The needle-free injection device according to claim 1, further comprising a gap-coupling connecting the rod of said piston and rod assembly to the plunger and being directly or indirectly connected to the nut of said charging mechanism, wherein said gap-coupling is configured to maintain a gap-distance between said rod and said plunger when said piston and rod assembly is in said rearward position.

7. The needle-free injection device according to claim 6, further comprising a plate member connecting said nut to said gap-coupling, wherein movement of said nut from a forward position to a rearward position along said length of the threaded shaft causes a corresponding movement of said plate member and said gap-coupling.

8. The needle-free injection device according to claim 7, wherein the gap-coupling comprises a first end for sliding engagement with the plunger and sized to slidingly fit within a passage of the plate member, and a second end for removable attachment of the gap-coupling to said rod and sized such that it does not fit within the passage of said plate member.

9. The needle-free injection device according to claim 1, further comprising rotation means for rotating said threaded shaft.

10. The needle-free injection device according to claim 9, wherein said rotation means are motorized or manual.

11. The needle-free injection device according to claim 10, wherein said motorized means are a non-rechargeable DC power supply, a rechargeable DC power supply, or an AC power supply.

12. The needle-free injection device according to claim 10 wherein said manual means is a hand crank.

13. The needle-free injection device according to claim 1, wherein the threaded shaft is a lead screw.

14. The needle-free injection device according to claim 13, further comprising a ball bearing run in a larger threaded portion of said lead screw.

15. The needle-tree injection device according to claim 1, wherein the nut member is a ball nut.

16. The needle-free injector according to claim 9, wherein said rotation means comprises a two-way drive transmission.

17. The needle-free injector according to claim 16, wherein said two-way drive transmission is operatively associated with said threaded shaft via a gear assembly.

18. The needle-free injection device according to claim 1, wherein said trigger comprises a trigger plate including a locking passage through which a portion of the rod extends, said trigger plate movable between a locked position and an unlocked position, wherein in the unlocked position said locking passage is generally axially aligned with said rod to permit axial movement of the rod, and wherein in said locked position said trigger plate is generally out of axial alignment with said rod such that an inner surface of said locking passage is frictionally engaged with a surface of said rod thereby retaining said piston and rod assembly in said rearward position.

19. The needle-free injector according to claim 1, further comprising a metering mechanism for setting a desired dose of medicament to be delivered.

20. A method of injecting a medicament into an animal or a human, comprising:
(i) providing an actuated needle-free injection device according to claim 1 having a medicament within said dosing chamber;
(ii) placing the outlet orifice against said animal at a site for administration; and
(iii) triggering said injection device such that said medicament is expelled through said outlet orifice.

21. A kit for the use of the needle-free injection device according to claim 1 comprising;
(i) a needle free injection device according to claim 1; and
(ii) instructions for the use thereof.

22. Use of the needle-free injection device according to claim 1 for administering a medicament to a subject.

* * * * *